(12) United States Patent
Chen et al.

(10) Patent No.: US 10,131,918 B2
(45) Date of Patent: Nov. 20, 2018

(54) GENE FOR REGULATING THE FLORAL MORPHOLOGY OF AN ORCHID

(71) Applicant: National Pingtung University of Science and Technology, Neipu Township (TW)

(72) Inventors: Fure-Chyi Chen, Neipu Township (TW); Jian-Zhi Huang, Neipu Township (TW); Chen-Yu Lee, Neipu Township (TW); Ting-Chi Cheng, Neipu Township (TW); Shih-Wen Chin, Neipu Township (TW)

(73) Assignee: National Pingtung University of Science and Technology, Neipu Township (TW)

( * ) Notice: Subject to any disclaimer, the term of this patent is extended or adjusted under 35 U.S.C. 154(b) by 1055 days.

(21) Appl. No.: 14/307,072

(22) Filed: Jun. 17, 2014

(65) Prior Publication Data

US 2015/0184172 A1   Jul. 2, 2015

(30) Foreign Application Priority Data

Oct. 15, 2013   (TW) .............................. 102137217 A

(51) Int. Cl.
| | | |
|---|---|---|
| *C12N 15/29* | (2006.01) | |
| *C12N 15/11* | (2006.01) | |
| *C12N 15/82* | (2006.01) | |
| *A01H 5/02* | (2018.01) | |
| *C07K 14/415* | (2006.01) | |
| *C12Q 1/6895* | (2018.01) | |

(52) U.S. Cl.
CPC .............. *C12N 15/827* (2013.01); *A01H 5/02* (2013.01); *C07K 14/415* (2013.01); *C12N 15/11* (2013.01); *C12Q 1/6895* (2013.01)

(58) Field of Classification Search
None
See application file for complete search history.

(56) References Cited

PUBLICATIONS

Hsu et al., Plant Cell Physiol. 44(8): 783-794 (2003).*
GenBank Accession HM140843, added Jul. 7, 2010.*
Thiruvengadam et al. Acta Physiol Plant (2012) 34:1295-1302.*
Schlickeiser et al. "Western, Northern, and Southern Blotting." Basic Science Techniques in Clinical Practice (2007): 48-57.*
Thiruvengadam et al. (Acta Physiol Plant (2012) 34:1295-1302). (Year: 2012).*
Notice of Allowance issued in Taiwanese Patent Application No. 102137217; dated Feb. 6, 2015 (4 pages).

* cited by examiner

*Primary Examiner* — Mykola V. Kovalenko
*Assistant Examiner* — Charles Logsdon
(74) *Attorney, Agent, or Firm* — Osha Liang LLP

(57) ABSTRACT

An isolated nucleic acid includes a sequence selected from the group consisting of the following: (i) a first nucleotide sequence of SEQ ID NO.: 7, SEQ ID NO.: 3, SEQ ID NO.: 9, or SEQ ID NO.: 5; (ii) a second nucleotide sequence encoding the amino acid sequence of SEQ ID NO.: 6, SEQ ID NO.: 4, SEQ ID NO.: 8, or SEQ ID NO.: 10; and (iii) a third nucleotide sequence complementary to the first nucleotide sequence or the second nucleotide sequence.

3 Claims, 12 Drawing Sheets

Specification includes a Sequence Listing.

GENE FOR REGULATING THE FLORAL MORPHOLOGY OF AN ORCHID

CROSS REFERENCE

The non-provisional application claims priority from Taiwan Patent Application NO. 102137217, filed on Oct. 15, 2013, the content thereof is incorporated by reference herein.

FIELD OF THE INVENTION

The present invention relates to a novel gene from *Phalaenopsis* sp., and more specifically to the novel gene's relationship to the regulation of an orchid's floral morphology.

BACKGROUND OF THE INVENTION

An orchid is the largest and most diverse family of flowering plants. Since an orchid is graceful in its floral morphology and blooms for 1-4 months, this plant is considerably popular with the public and widely used in decorations. Additionally, an orchid is the largest flower for export in Taiwan.

A flowering plant usually has a sepal, a petal, a stamen, and a pistil in sequence from the outside to the inside of its flower. In view of molecular biology, the flower is developed following the so-called "ABC model." Expression of A genes characterizes the sepal; co-expression of A genes and B genes characterizes the petal; co-expression of B genes and C genes characterizes the stamen; expression of C genes characterizes the pistil. See Plant Mol Biol. 2000; 42(1): 115-49.

Although an orchid belongs to a flowering plant, its floral development is complicated without an explanation of the "ABC model." Generally, the floral morphology of an orchid is classified into the following three categories: wild type, big-lip mutant, and peloric mutant. An orchid with a wild type floral morphology is shown on the left side of FIGS. 1A-1C, and its flower has two petals, one lip, three sepals, and one gynostemium. The two petals are symmetrical with each other, and the lip is distinct from each petal. An orchid with a big-lip mutant floral morphology is shown on the right side of FIG. 1C, and its lip is petal-like as compared with that of the plant with a wild type floral morphology. An orchid with a peloric mutant floral morphology is displayed on the right side of FIGS. 1A-1B, and its petals or sepals are lip-like relative to those of the plant with a wild type floral morphology. The floral morphology may have an effect on the plant's commercial value. It usually takes 1-3 years to cultivate an orchid, and the plant's floral morphology is usually ascertained during the late stage of cultivation. For such reason, if an orchid's floral morphology is predicted at the early stage of cultivation, and the plant having a non-marketable floral morphology is thrown away, the cost of unnecessary cultivation, such as time, labor, and money, is saved.

SUMMARY OF THE INVENTION

A first aspect of the present invention is to provide an isolated nucleic acid including a sequence selected from the group comprising: (i) a first nucleotide sequence of SEQ ID NO.: 1, SEQ ID NO.: 7, SEQ ID NO.: 3, SEQ ID NO.: 9, or SEQ ID NO.: 5; (ii) a second nucleotide sequence encoding an amino acid sequence of SEQ ID NO.: 6, SEQ ID NO.: 2, SEQ ID NO.: 8, SEQ ID NO.: 4, or SEQ ID NO.: 10; and (iii) a third nucleotide sequence complementary to the first nucleotide sequence or the second nucleotide sequence.

A second aspect of the present invention is to provide an isolated protein encoded by the aforementioned nucleic acid.

A third aspect of the present invention is to provide a recombinant vector including the aforementioned nucleic acid.

A fourth aspect of the present invention is to provide a transgenic cell including the aforementioned recombinant vector.

A fifth aspect of the present invention is to provide a transgenic tissue including the aforementioned recombinant vector.

A sixth aspect of the present invention is to provide a method for regulating a floral morphology of an orchid. The method comprises the following step(s) of: changing an amount of a transcript comprising the aforementioned nucleic acid in the orchid.

A seventh aspect of the present invention is to provide a method for regulating a floral morphology of an orchid. The method comprises the following step(s) of: changing an amount of the aforementioned protein in the orchid.

An eighth aspect of the present invention is to provide a method for producing a transgenic orchid. The method comprises the following step(s) of: changing an amount of a transcript comprising the aforementioned nucleic acid in an orchid tissue; and culturing the orchid tissue to obtain the transgenic orchid.

A ninth aspect of the present invention is to provide a method for predicting a floral morphology of an orchid. The method comprises the following step(s) of: providing a biological sample taken from the orchid; detecting an amount of a transcript comprising the aforementioned nucleic acid in the biological sample; and determining the floral morphology of the orchid based on the amount of the transcript.

A tenth aspect of the present invention is to provide a method for predicting a floral morphology of an orchid. The method comprises the following step(s) of: providing a biological sample taken from the orchid; detecting an amount of the aforementioned protein in the biological sample; and determining the floral morphology of the orchid based on the amount of the protein.

An eleventh aspect of the present invention is to provide a primer pair comprising: a forward primer having a nucleotide sequence of SEQ ID NO.: 13; and a reverse primer having a nucleotide sequence of SEQ ID NO.: 14.

A twelfth aspect of the present invention is to provide a primer pair comprising: a forward primer having a nucleotide sequence of SEQ ID NO.: 15; and a reverse primer having a nucleotide sequence of SEQ ID NO.: 16.

DETAILED DESCRIPTION OF THE INVENTION

Figure 1A:
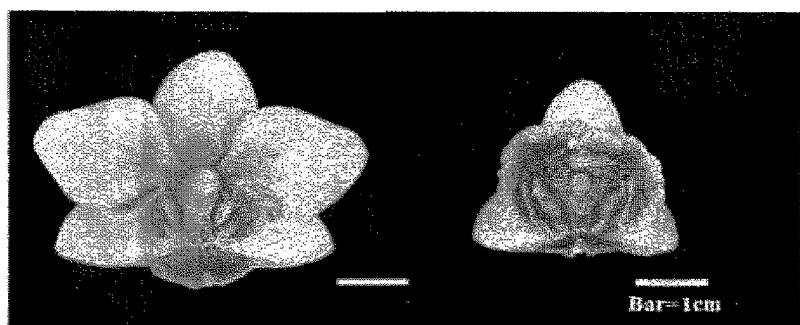
FIG. 1A is a picture presenting the flower of *Phalaenopsis* Brother Spring Dancer 'KHM190' with a wild type floral morphology, and that of *Phalaenopsis* Brother Spring Dancer 'KHM190' with a peloric mutant floral morphology.

The present invention is directed to a novel gene identified from *Phalaenopsis* sp., and the inventors call this gene "AGL6 gene". The present invention demonstrates the AGL6 gene is expressed to form a transcript in various forms and/or amounts so that the floral morphology of *Phalaenopsis* sp. is determined.

A first embodiment of the present invention discloses an isolated nucleic acid. The nucleic acid comprises a sequence selected from the group comprising: (i) a first nucleotide sequence of SEQ ID NO.: 1, SEQ ID NO.: 7, SEQ ID NO.: 3, SEQ ID NO.: 9, or SEQ ID NO.: 5; (ii) a second nucleotide sequence encoding an amino acid sequence of SEQ ID NO.: 6, SEQ ID NO.: 2, SEQ ID NO.: 8, SEQ ID NO.: 4, or SEQ ID NO.: 10; and (iii) a third nucleotide sequence complementary to the first nucleotide sequence or the second nucleotide sequence.

The first nucleotide sequence is firstly discussed. The sequence of SEQ ID NO.: 1 has 904 nucleotides; its coding sequence, encoding an amino acid sequence of 240 amino acids (SEQ ID NO.: 2), consists of the nucleotides 1-720. The sequence of SEQ ID NO.: 3 has 730 nucleotides; its coding sequence, encoding an amino acid sequence of 163 amino acids (SEQ ID NO.: 4), consists of the nucleotides 1-489. The sequence of SEQ ID NO.: 5 has 694 nucleotides; its coding sequence, encoding an amino acid sequence of 149 amino acids (SEQ ID NO.: 6), consists of the nucleotides 1-447. The sequence of SEQ ID NO.: 7 has 599 nucleotides; its coding sequence, encoding an amino acid sequence of 31 amino acids (SEQ ID NO.: 8), consists of the nucleotides 1-93. The sequence of SEQ ID NO.: 9 has 574 nucleotides; its coding sequence, encoding an amino acid sequence of 109 amino acids (SEQ ID NO.: 10), consists of the nucleotides 1-327. It is the first time that all sequences of SEQ ID NOS.: 1, 3, 5, 7, and 9 are isolated from the cDNA pools of *Phalaenopsis* sp. by the inventors. Specifically, the sequence of SEQ ID NO.: 1 is taken from the cDNA pools of *Phalaenopsis* sp. with a wild type floral morphology or those with a peloric mutant floral morphology, and the sequences of SEQ ID NOS.: 2, 4, 6, 8, and 10 are obtained from the cDNA pools of *Phalaenopsis* sp. with a big-lip mutant floral morphology. After alignment, the sequences of SEQ ID NOS.: 3, 5, 7, and 9 have a 100%-identity with respect to that of SEQ ID NO.: 1. As described above, the AGL6 gene is transcribed into an alternative spliced transcript including one sequence of SEQ ID NOS.: 1, 3, 5, 7, and 9 in *Phalaenopsis* sp., and the plant's floral morphology is characterized by such spliced transcript.

The second nucleotide sequence is secondly discussed. Because a transcript including one sequence of SEQ ID NOS.: 1, 3, 5, 7, and 9 can determine the floral morphology of *Phalaenopsis* sp., and the amino acid sequences of SEQ ID NOS.: 2, 4, 6, 8, and 10 are encoded by the sequences of SEQ ID NOS.: 1, 3, 5, 7, and 9, respectively, the AGL6 gene is translated into a protein including one sequence of SEQ ID NOS.: 2, 4, 6, 8, and 10 in the plant such that the protein can characterize the plant's floral morphology. With codon usage in plant genes, the nucleotide sequence encoding one sequence of SEQ ID NOS.: 2, 4, 6, 8, and 10 is not limited to each coding sequence previously described. Desirably, the coding sequence of SEQ ID NO.: 1 and its degenerate sequence both encode the sequence of SEQ ID NO.: 2; the coding sequence of SEQ ID NO.: 3 and its degenerate sequence both encode the sequence of SEQ ID NO.: 4; the coding sequence of SEQ ID NO.: 5 and its degenerate sequence both encode the sequence of SEQ ID NO.: 6; the coding sequence of SEQ ID NO.: 7 and its degenerate sequence both encode the sequence of SEQ ID NO.: 8; the coding sequence of SEQ ID NO.: 9 and its degenerate sequence both encode the sequence of SEQ ID NO.: 10. Accordingly, one sequence of SEQ ID NOS.: 1, 3, 5, 7, and 9 and its degenerate sequence are within the scope of the second nucleotide sequence.

The third nucleotide sequence is next discussed. The third nucleotide sequence is reasonably construed to accomplish the foregoing biological function of the first nucleotide sequence or the second nucleotide sequence, i.e. the characterization of a floral morphology of *Phalaenopsis* sp.

It is noted that the isolated nucleic acid is not only isolated from the natural world, e.g. *Phalaenopsis* sp., but also synthesized via genetic engineering techniques (Molecular Cloning: A Laboratory Manual, 4th Edi.) or chemical synthesis techniques (Tetrahedron Lett. 1983; 24(3): 245-48).

A second embodiment of the present invention discloses an isolated protein. The protein is encoded by the nucleic acid of the first embodiment. As what is described in the first embodiment, the protein at least comprises: an amino acid sequence of SEQ ID NO.: 6, SEQ ID NO.: 2, SEQ ID NO.: 8, SEQ ID NO.: 4, or SEQ ID NO.: 10, and the protein also can determine the floral morphology of *Phalaenopsis* sp.

It is noted that the isolated protein is not only isolated from the natural world, e.g. *Phalaenopsis* sp., but also synthesized via genetic engineering techniques (Molecular Cloning: A Laboratory Manual, 4th Edi.) or chemical synthesis techniques (Tetrahedron Lett. 1983; 24(3): 245-48).

A third embodiment of the present invention discloses a recombinant vector. The vector comprises the nucleic acid of the first embodiment. The vector may be transferred into a cell with the purpose of the nucleic acid replication or the protein production. The vector optionally requires a promoter operatively linked to the nucleic acid so that the promoter can up-regulate the nucleic acid to enhance the protein production.

A fourth embodiment of the present invention discloses a transgenic cell. The cell comprises the recombinant vector of the third embodiment. The cell can be used in nucleic acid replication or protein production on a large scale. The cell is, for example but not limited to, a prokaryotic cell or an eukaryotic cell, and preferably, an orchid cell.

A fifth embodiment of the present invention discloses a transgenic tissue. The tissue comprises the recombinant vector of the third embodiment. As described in the fourth embodiment, the tissue is also used to replicate the nucleic acid or produce the protein on a large scale. The tissue is, for example but not limited to, a seed, a protocorm, or a protocorm-like body of an orchid.

A sixth embodiment of the present invention discloses a method for regulating a floral morphology of an orchid. The method comprises: changing an amount of a transcript having the nucleic acid of the first embodiment in the orchid. In the embodiment, the regulated orchid is, for example but not limited to, *Phalaenopsis* sp. Also, details of the changing step are stated in the following parts:

1. If the nucleic acid of the first embodiment comprises: (i) the nucleotide sequence of SEQ ID NO.: 1, (ii) the nucleotide sequence encoding the amino acid sequence of SEQ ID NO.: 2, or (iii) the nucleotide sequence complementary to the (i) or (ii) nucleotide sequence, in the changing step, the changed amount is decreased to the extent that it is not null, and is equal to or less than a reference amount of the transcript in another orchid whose floral morphology is wild type. By such a way, the regulated orchid's floral morphology may be wild type.

2. In case the nucleic acid of the first embodiment comprises: (i) the nucleotide sequence of SEQ ID NO.: 1, (ii) the nucleotide sequence encoding the amino acid sequence of SEQ ID NO.: 2, or (iii) the nucleotide sequence complementary to the (i) or (ii) nucleotide sequence, in the changing step, the changed amount is increased to the extent that it is more than a reference amount of the transcript in another orchid whose floral morphology is wild type. In such a manner, the regulated orchid's floral morphology may be peloric mutant. Preferably, the recombinant vector of the third embodiment is transferred to the regulated orchid for the increased transcript amount. Generally, a means for the transferring process is practicable to people skilled in this art, e.g. gene gun, vacuum infiltration, pollen tube pathway, or *Agrobacterium*-mediated transformation.

3. When the nucleic acid of the first embodiment comprises: (i) one nucleotide sequence of SEQ ID NOS.: 3, 5, 7, and 9, (ii) the nucleotide sequence encoding one amino acid sequence of SEQ ID NOS.: 4, 6, 8, and 10, or (iii) the nucleotide sequence complementary to the (i) or (ii) nucleotide sequence, in the changing step, the amount is increased to the extent that it is not null. As such, the regulated orchid's floral morphology may be big-lip mutant. Preferably, the recombinant vector of the third embodiment is transferred to the regulated orchid for the transcript amount increasing. Generally, a means for the transferring process is practicable to people skilled in this art, e.g. gene gun, vacuum infiltration, pollen tube pathway, or *Agrobacterium*-mediated transformation.

A seventh embodiment of the present invention discloses a method for regulating a floral morphology of an orchid. The method comprises: changing an amount of the protein of the second embodiment in the orchid. In this embodiment, the regulated orchid is, for example but not limited to, *Phalaenopsis* sp. Additionally, details of the changing step are illustrated in the following parts:

1. If the protein of the second embodiment comprises the amino acid sequence of SEQ ID NO.: 2, in the changing step, the amount is repressed to the extent that it is not null, and is equal to or less than a reference amount of the protein in another orchid whose floral morphology is wild type. By such a way, the regulated orchid's floral morphology may be wild type.

2. In case the protein of the second embodiment comprises the amino acid sequence of SEQ ID NO.: 2, in the changing step, the amount is increased to the extent that it is more than a reference amount of the protein in another orchid whose floral morphology is wild type. As such, the regulated orchid's floral morphology may be peloric mutant. Preferably, the recombinant vector of the third embodiment is transferred to the regulated orchid for the increased amount. Generally, a means for the transferring step is practicable to people skilled in this art, e.g. gene gun, vacuum infiltration, pollen tube pathway, or *Agrobacterium*-mediated transformation.

3. Provided that the protein of the second embodiment comprises one amino acid sequence of SEQ ID NOS. 4, 6, 8, and 10, in the changing step, the amount is increased to the extent that it is not null. In such a way, the regulated orchid's floral morphology may be big-lip mutant. Preferably, the recombinant vector of the third embodiment is transferred to the regulated orchid to increase the protein amount. Generally, a means for the transferring step is practicable to people skilled in this art, e.g. gene gun, vacuum infiltration, pollen tube pathway, or *Agrobacterium*-mediated transformation.

An eighth embodiment of the present invention discloses a method for producing a transgenic orchid. The method comprises: changing an amount of a transcript comprising the nucleic acid of the first embodiment in an orchid tissue; and culturing the orchid tissue to obtain the transgenic orchid. In this embodiment, the orchid tissue is, for example but not limited to, a seed, a protocorm, or a protocorm-like body, and the orchid is, for example but not limited to, *Phalaenopsis* sp. Next, the culturing step is well-known to people skilled in the art. Also, details of the changing step are presented in the following parts:

1. If the nucleic acid of the first embodiment comprises: (i) the nucleotide sequence of SEQ ID NO.: 1, (ii) the nucleotide sequence encoding the amino acid sequence of SEQ ID NO.: 2, or (iii) the nucleotide sequence complementary to the (i) or (ii) nucleotide sequence, in the changing step, the amount is repressed to the extent that it is not null and is equal to or less than a reference amount of the transcript in another tissue of an orchid whose floral morphology is wild type. As such, the transgenic orchid's floral morphology may be wild type.

2. If the nucleic acid of the first embodiment comprises: (i) the nucleotide sequence of SEQ ID NO.: 1, (ii) the nucleotide sequence encoding the amino acid sequence of SEQ ID NO.: 2, or (iii) the nucleotide sequence complementary to the (i) or (ii) nucleotide sequence, in the changing step, the amount is increased to the extent that it is more than a reference amount of the transcript in another tissue of an orchid whose floral morphology is wild type. As such, the transgenic orchid's floral morphology may be peloric mutant. Preferably, the recombinant vector of the third embodiment is transferred to the changed orchid tissue for the increased amount. Generally, a means for the transferring step is practicable to people skilled in the art, e.g. gene gun, vacuum infiltration, pollen tube pathway, or *Agrobacterium*-mediated transformation.

3. If the nucleic acid of the first embodiment comprises: (i) one nucleotide sequence of SEQ ID NOS.: 3, 5, 7, and 9, (ii) the nucleotide sequence encoding one amino acid sequence of SEQ ID NOS.: 4, 6, 8, and 10, or (iii) the nucleotide sequence complementary to the (i) or (ii) nucleotide sequence, in the changing step, the amount is increased to the extent that it is not null. In such a manner, the transgenic orchid's floral morphology may be big-lip mutant. Preferably, the recombinant vector of the third embodiment is transferred to the orchid tissue for the amount increasing. Generally, a means for the transferring step is practicable to people skilled in the art, e.g. gene gun, vacuum infiltration, pollen tube pathway, or *Agrobacterium*-mediated transformation.

A ninth embodiment of the present invention discloses a method for predicting a floral morphology of an orchid. The method comprises: providing a biological sample taken from the orchid; detecting an amount of a transcript comprising the nucleic acid of the first embodiment in the biological sample; and determining the floral morphology of the orchid based on the amount of the transcript. In this embodiment, the biological sample is, for example but not limited to, a seed, a protocorm, or a protocorm-like body, and the orchid is, for example but not limited to, *Phalaenopsis* sp. Also, the detecting step may accomplish its purpose via, for example but not limited to, quantitative RT-PCR or Northern blotting. Next, details of the determining step are described in the following parts:

1. If the nucleic acid of the first embodiment comprises: (i) the nucleotide sequence of SEQ ID NO.: 1, (ii) the nucleotide sequence encoding the amino acid sequence of SEQ ID NO.: 2, or (iii) the nucleotide sequence complementary to the (i) or (ii) nucleotide sequence, in the determining step, the amount is compared with a reference amount of the transcript in another biological sample taken from an orchid whose floral morphology is wild type. If the detected amount is not null, and is equal to or less than the reference amount, the predicted orchid's floral morphology may be wild type. If the detected amount is more than the reference amount, the predicted orchid's floral morphology may be peloric mutant.

2. If the nucleic acid of the first embodiment comprises: (i) one nucleotide sequence of SEQ ID NOS.: 3, 5, 7, and 9, (ii) the nucleotide sequence encoding one amino acid sequence of SEQ ID NOS.: 4, 6, 8, and 10, or (iii) the nucleotide sequence complementary to the (i) or (ii) nucleotide sequence, in the determining step, the amount is analyzed to be null or not null. If the amount is not null, the predicted orchid's floral morphology may be big-lip mutant.

A tenth embodiment of the present invention discloses a method for predicting a floral morphology of an orchid. The method comprises: providing a biological sample taken from the orchid; detecting an amount of the protein of the second embodiment in the biological sample; and determining the floral morphology of the orchid based on the amount of the protein. In this embodiment, the biological sample is, for example but not limited to, a seed, a protocorm, or a protocorm-like body, and the orchid is, for example but not limited to, Phalaenopsis sp. Also, the detecting step may achieve the purposes via, for example but not limited to, ELISA or Western blotting. Next, details of the determining step are described in the following parts:

1. If the protein of the second embodiment comprises the amino acid sequence of SEQ ID NO.: 2, in the determining step, the amount is compared with a reference amount of the protein in another biological sample taken from an orchid whose floral morphology is wild type. When the detected amount is not null, and is equal to or less than the reference amount, the predicted orchid's floral morphology may be wild type. When the detected amount is more than the reference amount, the predicted orchid's floral morphology may be peloric mutant.

2. If the protein of the second embodiment comprises one amino acid sequence of SEQ ID NOS.: 4, 6, 8, and 10, in the determining step, the amount is analyzed to be null or not null. If the amount is not null, the predicted orchid's floral morphology may be big-lip mutant.

An eleventh embodiment of the present invention discloses a primer pair. The primer pair comprises: a forward primer provided with a nucleotide sequence of SEQ ID NO.: 13; and a reverse primer provided with a nucleotide sequence of SEQ ID NO.: 14. These primers are located at part fragments of the nucleotide sequences of SEQ ID NOS.: 1, 3, 5, 7, and 9, and are able to be employed to amplify all the sequences. As such, the primer pair may be in use of quantitative RT-PCR of the ninth embodiment in order to detect the amount of the transcript, and further to predict the floral morphology of the orchid.

A twelfth embodiment of the present invention discloses a primer pair. The primer pair comprises: a forward primer provided with a nucleotide sequence of SEQ ID NO.: 15; and a reverse primer provided with a nucleotide sequence of SEQ ID NO.: 16. The two primers are partially located at the nucleotide sequences of SEQ ID NOS.: 1, 3, 5, 7, and 9, and can be introduced to amplify all of the sequences. In such a manner, the primer pair may be in use of quantitative RT-PCR of the ninth embodiment to detect the amount of the transcript, and further to predict the floral morphology of the orchid.

The following examples are offered to further illustrate these embodiments of the invention.

Example 1

Culture of Phalaenopsis sp.

From left to right in FIG. 1A are the flower of Phalaenopsis Brother Spring Dancer 'KHM190' with a wild type floral morphology, and that of Phalaenopsis Brother Spring Dancer 'KHM190' with a peloric mutant floral morphology. The petals shown in the right column are clearly lip-like.

Figure 1B:
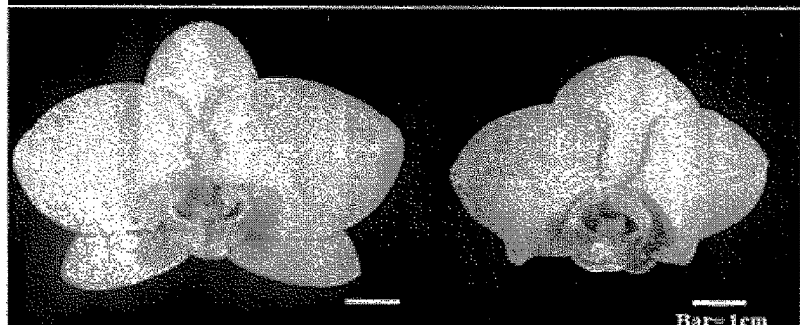
FIG. 1B is a picture showing the flower of *Phalaenopsis amabilis* with a wild type floral morphology, and that of *Phalaenopsis amabilis* with a peloric mutant floral morphology.

From left to right in FIG. 1B are the flower of Phalaenopsis amabilis with a wild type floral morphology, and that of Phalaenopsis amabilis with a peloric mutant floral morphology. The sepals shown in the right column are clearly lip-like.

Figure 1C:
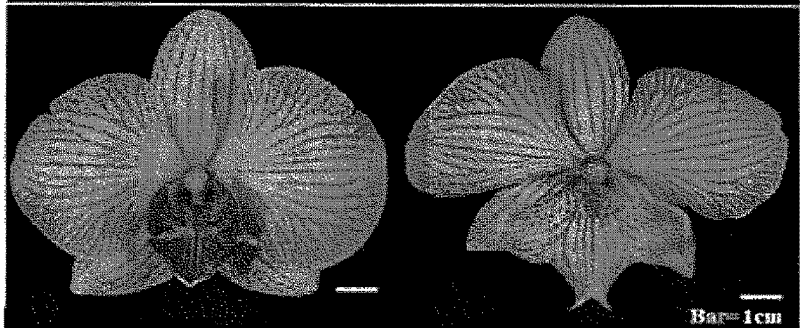
FIG. 1C is a picture displaying the flower of *Phalaenopsis* '98201' with a wild type floral morphology, and that of *Phalaenopsis* 'NPU-1459' with a big-lip mutant floral morphology.

From left to right in FIG. 1C are the flower of Phalaenopsis '98201' with a wild type floral morphology, and that of Phalaenopsis 'NPU-1459' with a big-lip mutant floral morphology. The lip shown in the right column is clearly petal-like.

All the plants were cultivated in a water-wall greenhouse irradiated with skylight at a temperature of 26-30'C, and then their flowers were picked.

Example 2

Identification of a Wild Type Transcript of Phalaenopsis AGL6 Gene

Floral organs of Phalaenopsis '98201' with a wild type floral morphology, including a sepal (divided into a top sepal and a bottom sepal), a petal, a lip and a gynostemium, were selected, and then total RNA therein was extracted following the process in Cell Res. 2005; 15: 639-57.

According to the manual of SMART RACE cDNA Amplification kit (Clontech), RT-PCR was practiced to amplify 1 μg of total RNA in each organ so as to gain a 5'-RACE-Ready cDNA and a 3'-RACE-Ready cDNA. Following the same manual, an AGL6GSP1 primer (SEQ ID NO.: 11) was introduced to amplify the 5'-RACE-Ready cDNA, and an AGL6GSP2 primer (SEQ ID NO.: 12) was used to amplify the 3'-RACE-Ready cDNA.

After the amplified product was ligated to a pGEM-T EASY vector (Promega), the ligated product was transformed to E. coli INVαF. A bacterial with a plasmid containing the amplified product was screened by X-gal and PCR. An AGLeteF primer (SEQ ID NO.: 13) and an AGLeteR primer (SEQ ID NO.: 14) were employed to sequence the plasmid. After which, the sequence of a wild type cDNA (SEQ ID NO.: 1) of AGL6 gene was obtained.

Accordingly, the wild type transcript of Phalaenopsis AGL6 gene at least comprises the sequence of SEQ ID NO.: 1. After the prediction by DNA STAR Editseq™ expert sequence analysis, the sequence of SEQ ID NO.: 1 encodes an amino acid sequence of 240 amino acids (SEQ ID NO: 2). In other words, a wild protein of Phalaenopsis AGL6 gene has the sequence of 240 amino acids.

Figure 2:
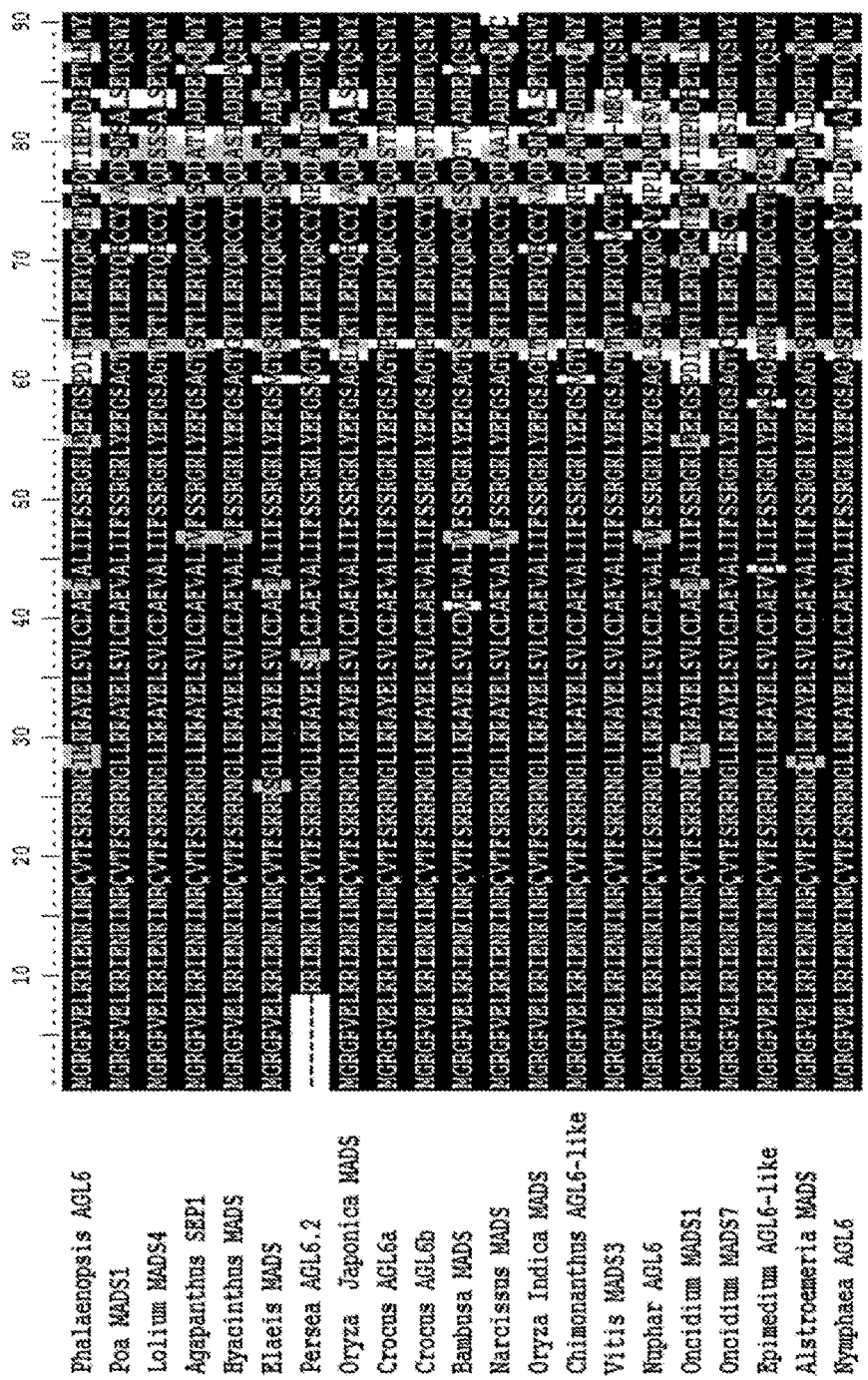
FIG. 2 is a BLAST result showing amino acid sequence alignments between wild type protein of *Phalaenopsis* sp. AGL6 gene (SEQ ID NO: 6) and proteins of other species' genes, e.g., *Poa* MADS1 (SEQ ID NO: 19), *Lolium* MADS4 (SEQ ID NO: 20), *Agapanthus* SEP 1 (SEQ ID NO: 21), *Hyacinthus* MADS (SEQ ID NO: 22), *Elaeis* MADS (SEQ ID NO: 23), *Persea* AGL6.2 (SEQ ID NO: 24), *Oryza Japonica* MADS (SEQ ID NO: 25), *Crocus* AGL6a (SEQ ID NO: 26), *Crocus* AGL6b (SEQ ID NO: 27), *Bambusa* MADS (SEQ ID NO: 28), *Narcissus* MADS (SEQ ID NO: 29), *Oryza Indica* MADS (SEQ ID NO: 30), *Chimonanthus* AGL6-like (SEQ ID NO: 31), *Vitis* MADS3 (SEQ ID NO: 32), *Nuphar* AGL6 (SEQ ID NO: 33), *Oncidium* MADS7 (SEQ ID NO: 34), *Oncidium* MADS7 (SEQ ID NO: 35), *Epimedium* AGL6-like (SEQ ID NO: 36), *Alstroemeria* MADS (SEQ ID NO: 37), and *Nymphaea* AGL6 (SEQ ID NO: 38).
Figure 2:
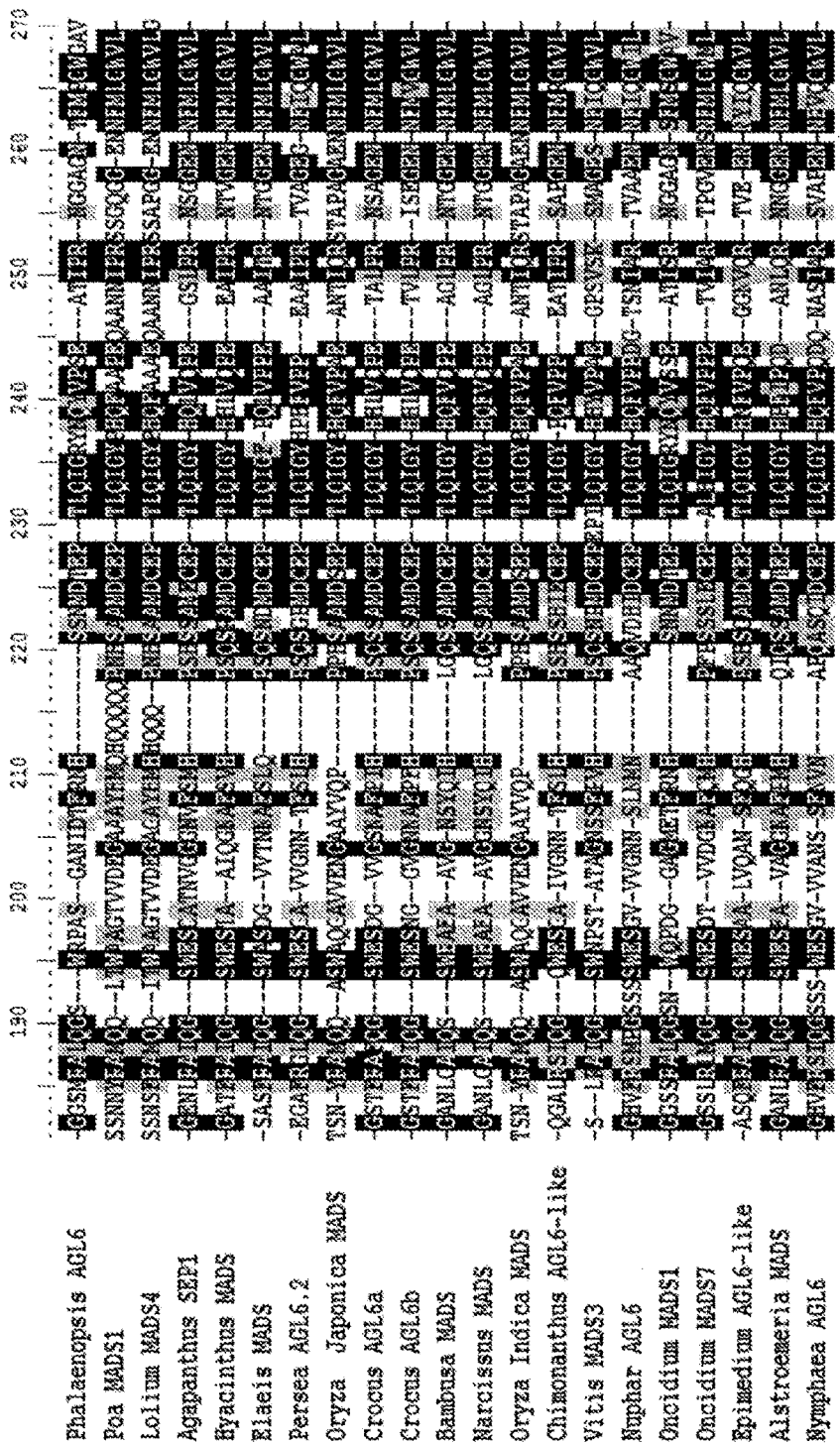

As shown in FIG. 2, a BLAST result shows amino acid sequence alignments between wild type protein of Phalaenopsis sp. AGL6 gene (SEQ ID NO: 6) and proteins of other species' genes, e.g., Poa MADS1 (SEQ ID NO: 19), Lolium MADS4 (SEQ ID NO: 20), Agapanthus SEP1 (SEQ ID NO: 21), Hyacinthus MADS (SEQ ID NO: 22), Elaeis MADS (SEQ ID NO: 23), Persea AGL6.2 (SEQ ID NO: 24), Oryza Japonica MADS (SEQ ID NO: 25), Crocus AGL6a (SEQ ID NO: 26), Crocus AGL6b (SEQ ID NO: 27), Bambusa MADS (SEQ ID NO: 28), Narcissus MADS (SEQ ID NO: 29), Oryza Indica MADS (SEQ ID NO: 30), Chimonanthus AGL6-like (SEQ ID NO: 31), Vitis MADS3 (SEQ ID NO: 32), Nuphar AGL6 (SEQ ID NO: 33), Oncidium MADS1 (SEQ ID NO: 34), Oncidium MADS7 (SEQ ID NO: 35), Epimedium AGL6-like (SEQ ID NO: 36), Alstroemeria MADS (SEQ ID NO: 37), and Nymphaea AGL6 (SEQ ID NO: 38). The figure suggests that the wild type protein of Phalaenopsis sp. AGL6 gene (SEQ ID NO: 6) has a 90%-similarity relative to the protein of Oncidium MADS1 gene (SEQ ID NO: 34).

Figure 3:
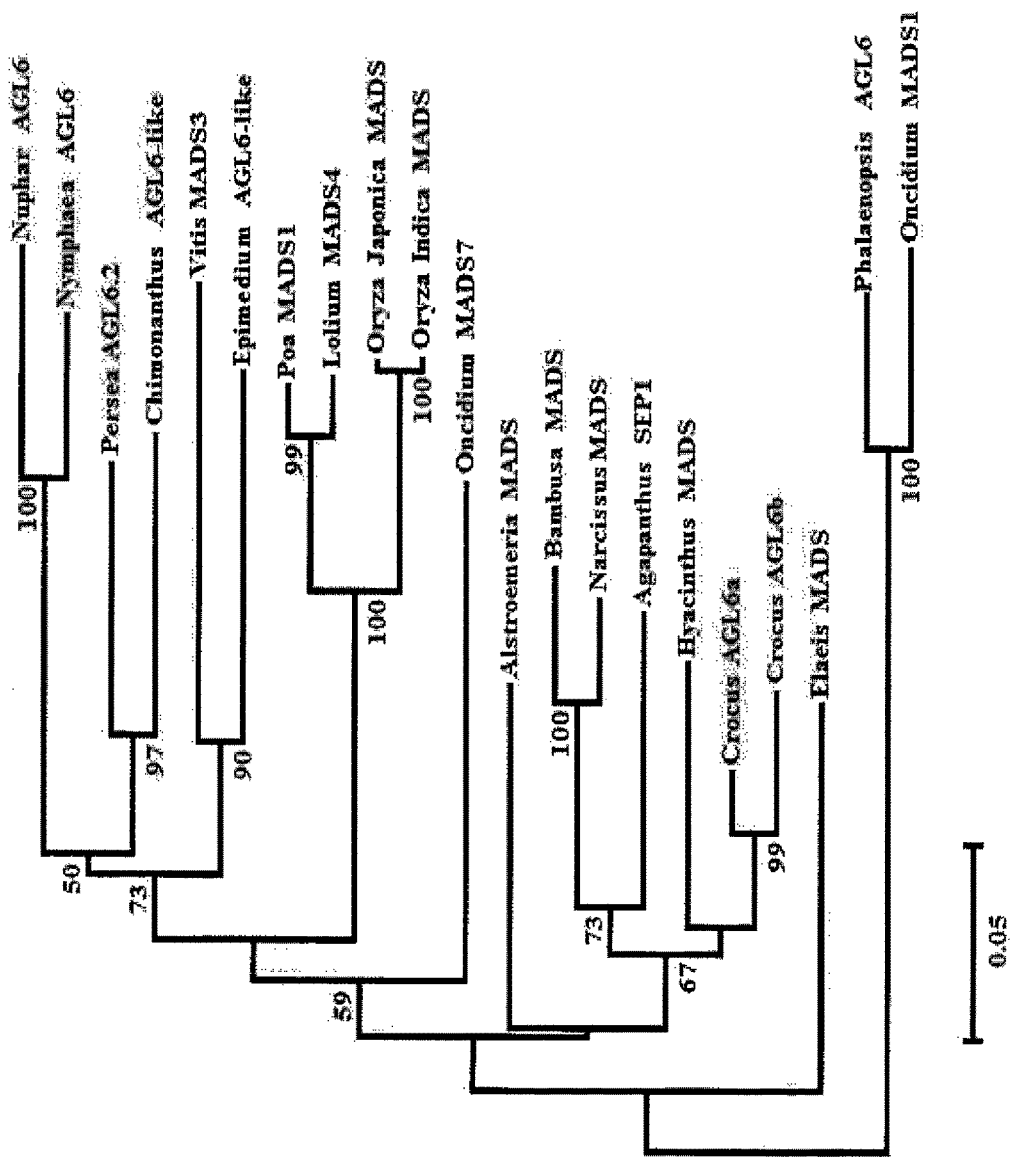
FIG. 3 is a phylogenetic tree presenting the relationship between a wild type protein of *Phalaenopsis* AGL6 gene and proteins of other species' genes.

As shown in FIG. 3, a phylogenetic tree shows the relationship between the wild type protein of Phalaenopsis AGL6 gene and proteins of other species' genes, and the tree is constructed by Neighbor-Joining method of MEGA 5.

According to the figure, the wild type protein of *Phalaenopsis* AGL6 gene is very close to the protein of *Oncidium* MADS1 gene.

Example 3

Expression Level of a Wild Type Transcript of *Phalaenopsis* AGL6 Gene

In this example, quantitative RT-PCR was applied to detect the expression level of a wild type transcript of *Phalaenopsis* AGL6 gene in each floral organ. Based on the manual of SMART PCR cDNA Synthesis kit, 1 mg of total RNA in each organ was amplified by RT-PCR to form a first cDNA. Then, a real-AGL6-F primer (SEQ ID NO.: 15) and a real-AGL6-R primer were introduced to amplify the first cDNA so as to obtain a wild type cDNA of *Phalaenopsis* AGL6 gene, and a PhActr-F primer (SEQ ID NO.: 17) and a PhActr-R primer (SEQ ID NO.: 18) were used to amplify the first cDNA so as to obtain a cDNA of Actin gene. Finally, the luminous intensities of the two cDNA products were employed to calculate the expression level of the wild type transcript of *Phalaenopsis* AGL6 gene.

Figure 4A:
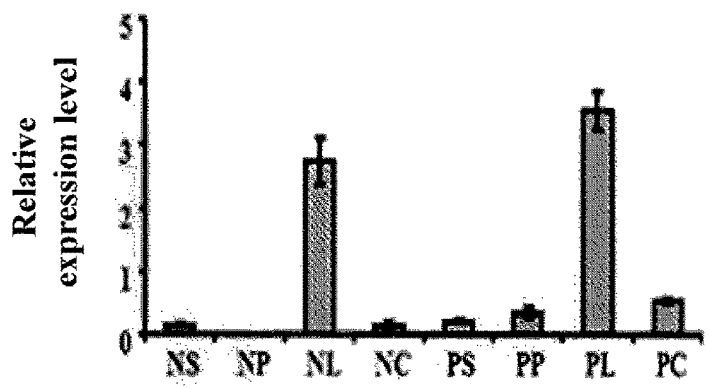
FIG. 4A is a quantitative RT-PCR result illustrating the expression level of a wild type transcript of *Phalaenopsis* AGL6 gene in each floral organ of *Phalaenopsis* Brother Spring Dancer 'KHM190' with a wild type floral morphology, and that in each floral organ of *Phalaenopsis* Brother Spring Dancer 'KHM190' with a peloric mutant floral morphology. All abbreviations therein are as follows: NS, a sepal of the plant with a wild type floral morphology; NP, a petal of the plant with a wild type floral morphology; NL, a lip of the plant with a wild type floral morphology; NC, a gynostemium of the plant with a wild type floral morphology; PS, a sepal of the plant with a peloric mutant floral morphology; PP, a petal of the plant with a peloric mutant floral morphology; PL, a lip of the plant with a peloric mutant floral morphology; and PC, a gynostemium of the plant with a peloric mutant floral morphology.

As shown in FIG. 4A, the expression level of the wild type transcript of *Phalaenopsis* AGL6 gene in the lip of *Phalaenopsis* Brother Spring Dancer 'KHM190' with a wild type floral morphology, and that in the lip of *Phalaenopsis* Brother Spring Dancer 'KHM190' with a peloric mutant floral morphology are detected, and the latter is higher than the former.

Figure 4B:
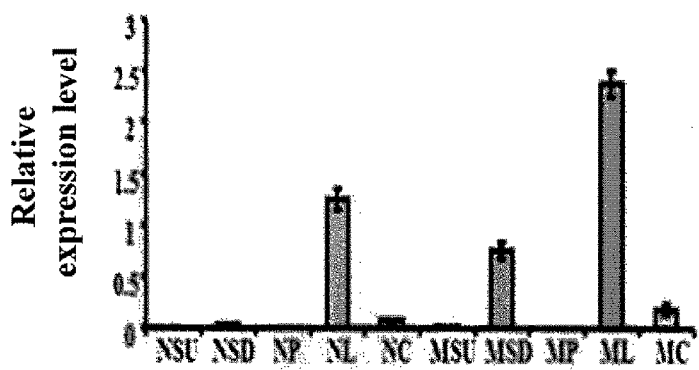
FIG. 4B is a quantitative RT-PCR result demonstrating the expression level of a wild type transcript of *Phalaenopsis* AGL6 gene in each floral organ of *Phalaenopsis amabilis* with a wild type floral morphology, and that in each floral organ of *Phalaenopsis amabilis* with a peloric mutant floral morphology. All abbreviations therein are as follows: NSU, a top sepal of the plant with a wild type floral morphology; NSD, a bottom sepal of the plant with a wild type floral morphology; NP, a petal of the plant with a wild type floral morphology; NL, a lip of the plant with a wild type floral morphology; NC, a gynostemium of the plant with a wild type floral morphology; MSU, a top sepal of the plant with a peloric mutant floral morphology; MSD, a bottom sepal of the plant with a peloric mutant floral morphology; MP, a petal of the plant with a peloric mutant floral morphology; ML, a lip of the plant with a peloric mutant floral morphology; and MC, a gynostemium of the plant with a peloric mutant floral morphology.

As shown in FIG. 4B, the expression level of the wild type transcript of *Phalaenopsis* AGL6 gene in the lip of *Phalaenopsis amabilis* with a wild type floral morphology, and that in the lip of *Phalaenopsis amabilis* with a peloric mutant floral morphology are measured, and the latter is high relative to the former.

Figure 4C:
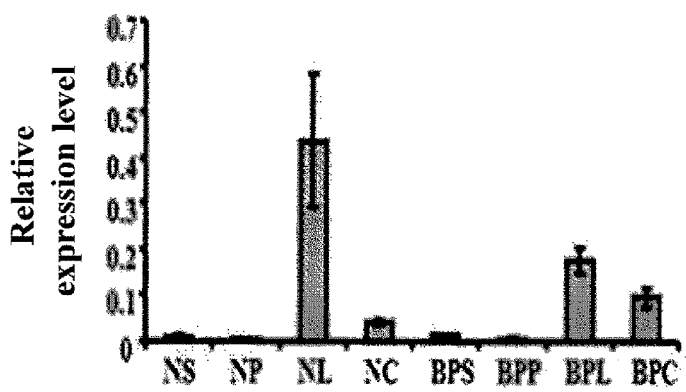
FIG. 4C is a quantitative RT-PCR result showing the expression level of a wild type transcript of *Phalaenopsis* AGL6 gene in each floral organ of *Phalaenopsis* '98201' with a wild type floral morphology, and that in each floral organ of *Phalaenopsis* 'NPU-1459' with a big-lip mutant floral morphology. All abbreviations therein are listed as follows: NS, a sepal of the plant with a wild type floral morphology; NP, a petal of the plant with a wild type floral morphology; NL, a lip of the plant with a wild type floral morphology; NC, a gynostemium of the plant with a wild type floral morphology; BPS, a sepal of the plant with a big-lip mutant floral morphology; BPP, a petal of the plant with a big-lip mutant floral morphology; BPL, a lip of the plant with a big-lip mutant floral morphology; and BPC, a gynostemium of the plant with a big-lip mutant floral morphology.

As shown in FIG. 4C, the expression level of the wild type transcript of *Phalaenopsis* AGL6 gene in the lip of *Phalaenopsis* '98201' with a wild type floral morphology, and that in the lip of *Phalaenopsis* 'NPU-1459' with a big-lip mutant floral morphology are found, and the latter is larger than the former.

Figures 5A, 5B:
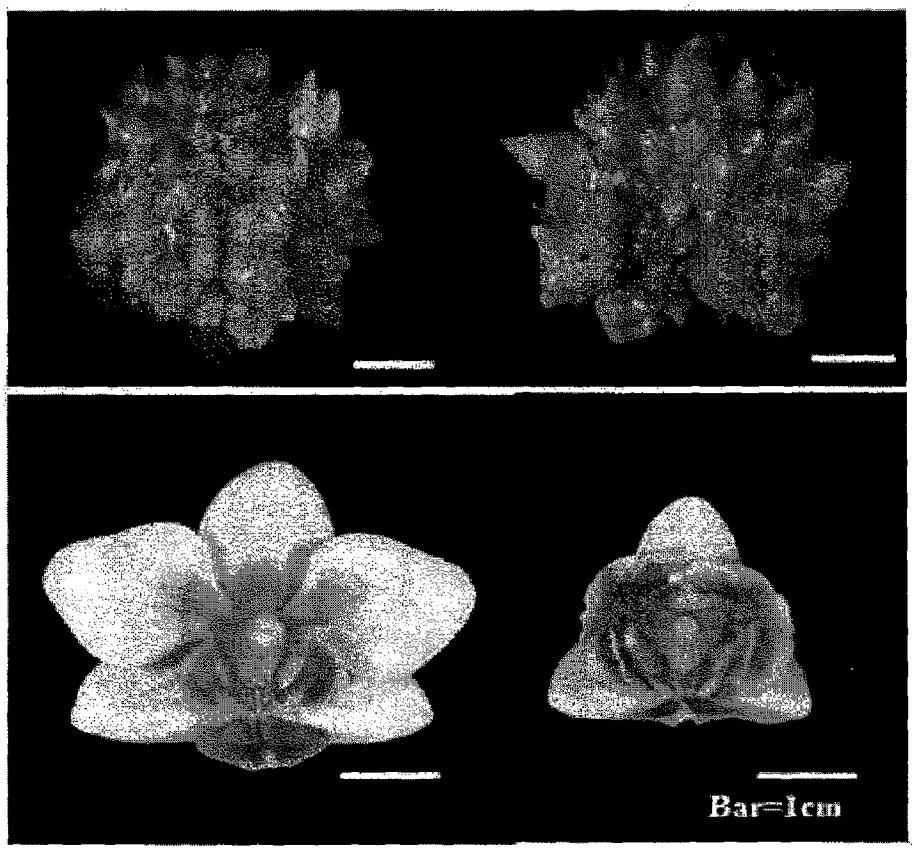
FIG. 5A is a picture showing the protocorm-like body of *Phalaenopsis* Brother Spring Dancer 'KHM190' with a wild type floral morphology, and that of *Phalaenopsis* Brother Spring Dancer 'KHM190' with a peloric mutant floral morphology.
FIG. 5B is a picture showing the flower of *Phalaenopsis* Brother Spring Dancer 'KHM190' with a wild type floral morphology, and that of *Phalaenopsis* Brother Spring Dancer 'KHM190' with a peloric mutant floral morphology.
Figure 5C:
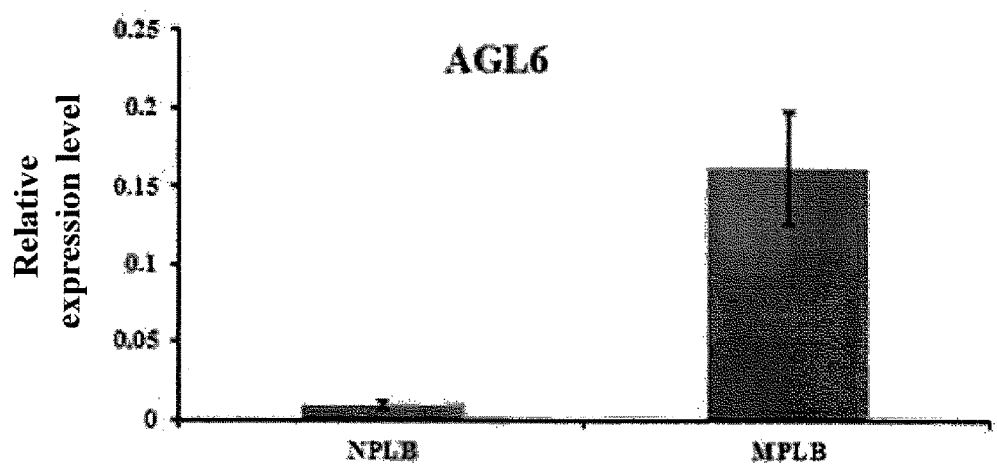
FIG. 5C is a quantitative RT-PCR result demonstrating the expression level of a wild type transcript of *Phalaenopsis* AGL6 gene in a protocorm-like body of *Phalaenopsis* Brother Spring Dancer 'KHM190' with a wild type floral morphology, and that in a protocorm-like body of *Phalaenopsis* Brother Spring Dancer 'KHM190' with a peloric mutant floral morphology. All abbreviations therein are as follows: NPLB, the protocorm-like body of the plant with a wild type floral morphology; and MPLB, the protocorm-like body of the plant with a peloric mutant floral morphology.

As described above, if the amount of the wild type transcript of *Phalaenopsis* AGL6 gene in the plant's non-floral organ is still similar to the foregoing outcome, the amount in the non-floral organ may be used as a basis for predicting the floral morphology of the plant. From left to right in FIG. 5A are the protocorm-like body of *Phalaenopsis* Brother Spring Dancer 'KHM190' with a wild type floral morphology, and that of *Phalaenopsis* Brother Spring Dancer 'KHM190' with a peloric mutant floral morphology, and they are alike. In contrast, from left to right in FIG. 5B are the flower of *Phalaenopsis* Brother Spring Dancer 'KHM190' with a wild type floral morphology, and that of *Phalaenopsis* Brother Spring Dancer 'KHM190' with a peloric mutant floral morphology, and they are distinct. Herein, the foregoing method for obtaining total RNA and the foregoing method for detecting to the amount of the wild type transcript of *Phalaenopsis* AGL6 gene in each floral organ are practiced to detect the amount of the wild type transcript of *Phalaenopsis* AGL6 gene in the protocorm-like body of *Phalaenopsis* Brother Spring Dancer 'KHM190' with a wild type floral morphology, and that in the protocorm-like body of *Phalaenopsis* Brother Spring Dancer 'KHM190' with a peloric mutant floral morphology. The detecting result is shown in FIG. 5C, and the amount of the wild type transcript of *Phalaenopsis* AGL6 gene in the protocorm-like body of *Phalaenopsis* Brother Spring Dancer 'KHM190' with a wild type floral morphology is lower than that in the protocorm-like body of *Phalaenopsis* Brother Spring Dancer 'KHM190' with a peloric mutant floral morphology. This illustrates that the amount of the wild type transcript of *Phalaenopsis* AGL6 gene in a non-floral organ of the plant can be used to predict the plant's floral morphology is wild type or peloric mutant.

Example 4

Identification of a Mutant Transcript of *Phalaenopsis* AGL6 Gene

In this example, RT-PCR was applied to identify a mutant transcript of *Phalaenopsis* AGL6 gene. With reference to the manual of SMART PCR cDNA Synthesis kit, 1 mg of total RNA in each floral organ was amplified by RTPCR to form a first cDNA. Then, an AGLeteF primer (SEQ ID NO.: 13) and an AGLeteR primer (SEQ ID NO.: 14) were employed to amplify the first cDNA so as to obtain a cDNA of *Phalaenopsis* AGL6 gene. Finally, the transcript was ascertained to be wild type or mutant by using the DNA electrophoresis.

Figure 6:
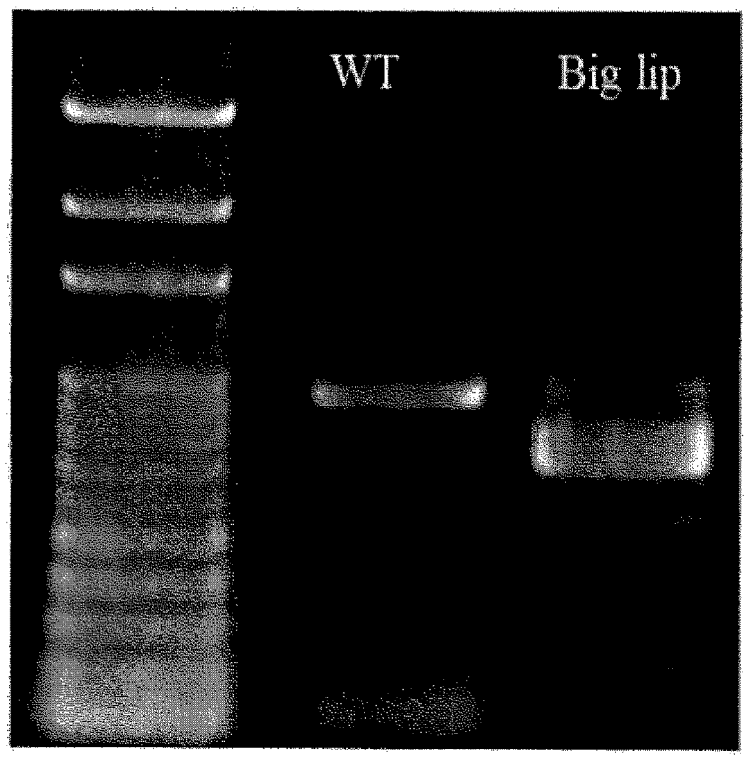
FIG. 6 is a DNA electropherogram showing a wild type transcript of *Phalaenopsis* AGL6 gene and a mutant transcript thereof. All abbreviations therein are as follows: WT, a lip of *Phalaenopsis* '98201' with a wild type floral morphology; Big lip, a lip of *Phalaenopsis* 'NPU-1459' with a big-lip mutant floral morphology.
Figure 7:
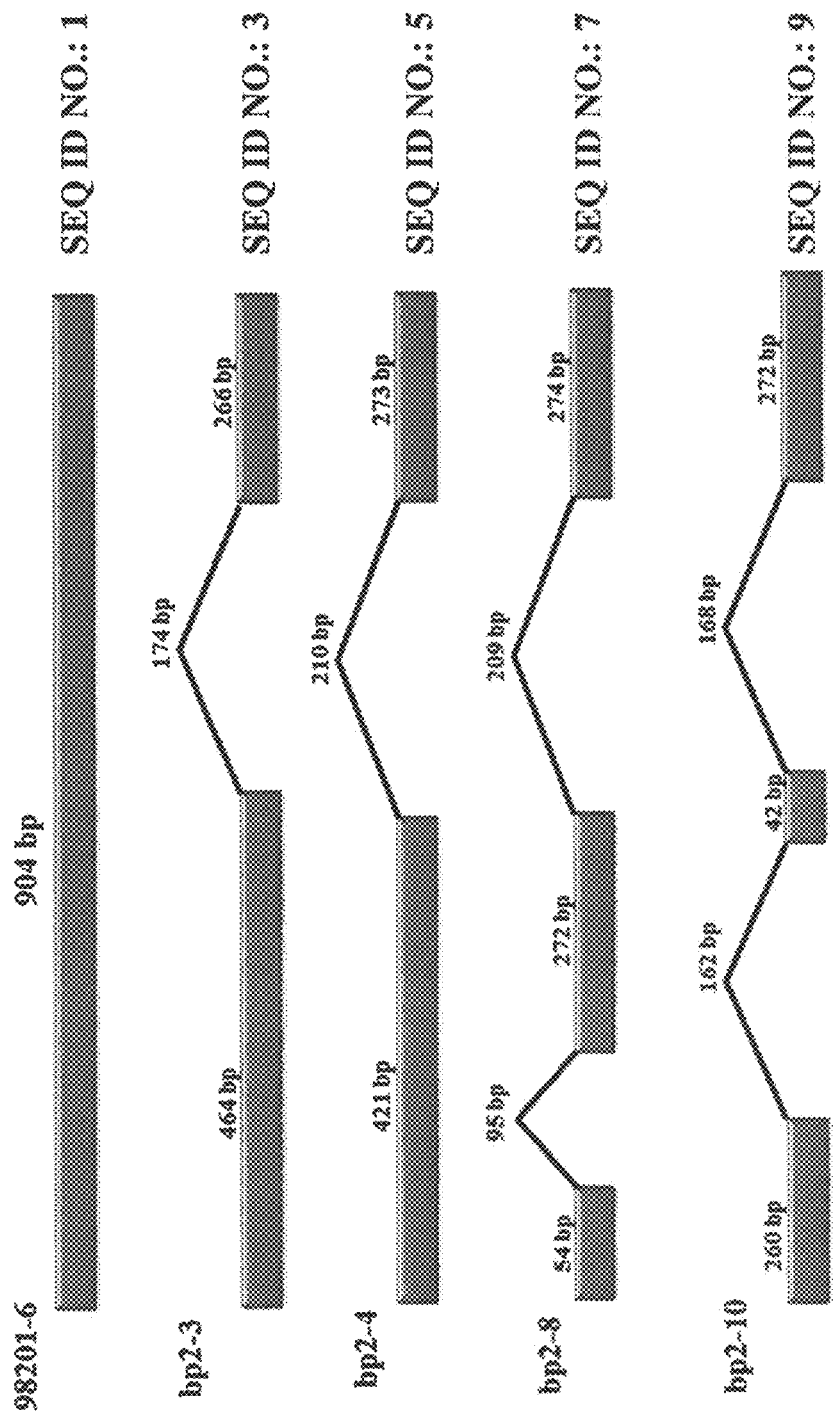
FIG. 7 is a sequence alignment illustrating the comparison between the sequence of a wild type transcript of *Phalaenopsis* AGL6 gene and that of a mutant transcript thereof.

As shown in FIG. 6, the transcript of *Phalaenopsis* AGL6 gene in the lip of *Phalaenopsis* '98201' with a wild type floral morphology is wild type; however, that in the lip of *Phalaenopsis* 'NPU-1459' with a big-lip mutant floral morphology is mutant, and this mutant transcript at least includes any one sequence of SEQ ID NOS.: 3, 5, 7, and 9. The sequence of the wild type transcript and the sequences of the mutant transcript are aligned as shown in FIG. 7.

Figure 8A:
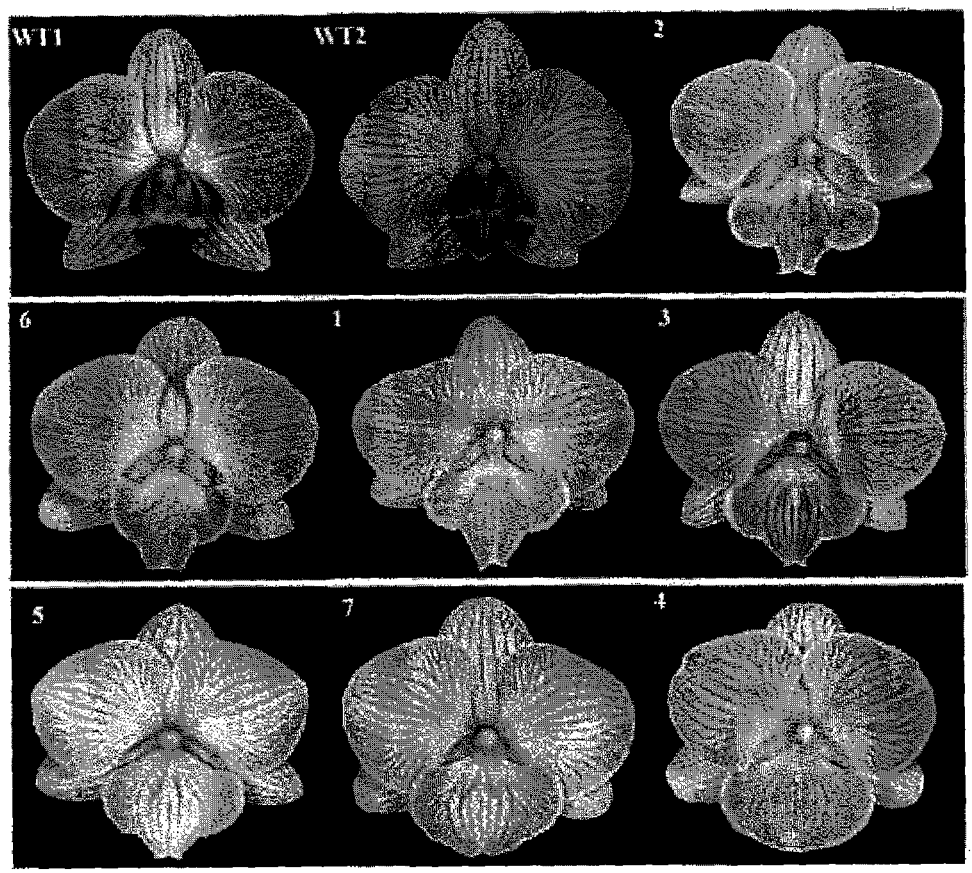
FIG. 8A is a picture showing the flowers of *Phalaenopsis* '98201' with a wild type floral morphology, numbered as WT1 and WT2 respectively, and those of *Phalaenopsis* 'NPU-1459' with a big-lip mutant floral morphology, numbered as 1-7 respectively.
Figure 8B:
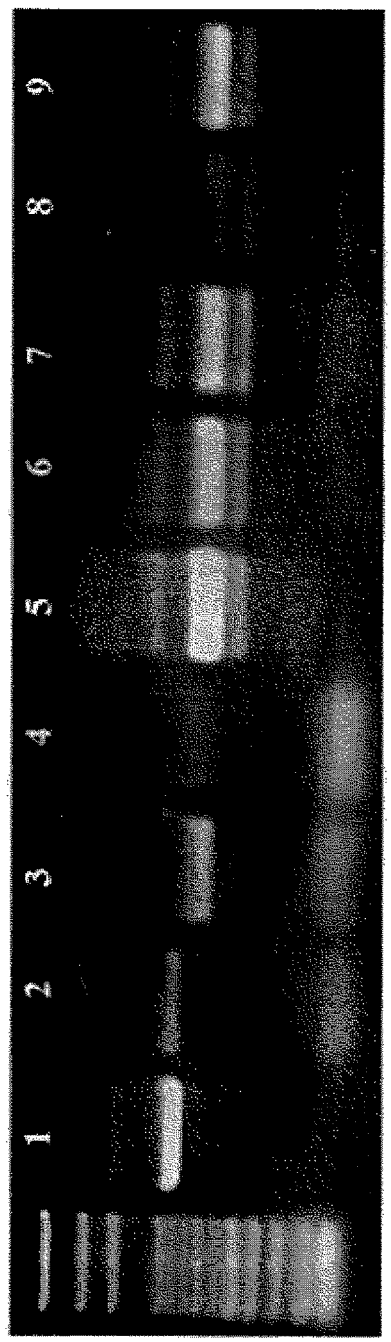
FIG. 8B is a DNA electropherogram determining a transcript of *Phalaenopsis* AGL6 gene in the lip of each plant shown in FIG. 8A is wild type or mutant. All the lines are as follows: line 1, the flower as WT1; line 2, the flower as WT2; line 3, the flower as 2; line 4, the flower as 6; line 5, the flower as 1; line 6, the flower as 3; line 7, the flower as 5; line 8, the flower as 7; and line 9, the flower as 4.

To further confirm the result shown in FIG. 6, two flowers of *Phalaenopsis* '98201' with a wild type floral morphology, numbered as WT1 and WT2 respectively, and seven flowers of *Phalaenopsis* 'NPU-1459' with a big-lip mutant floral morphology, numbered as 1-7 respectively, were taken (FIG. 8A), and the transcript in each flower's lip was determined to be wild type or mutant following the previously described method. As shown in FIG. 8B, the transcripts in the lips of the plants with a wild type floral morphology are both wild type, and all the transcripts in the lips of the plants with a big-lip mutant floral morphology are mutant. As such, the result in FIG. 6 is reproducible.

While the invention has been described in connection with what is considered the most practical and preferred embodiments, it is understood that this invention is not limited to the disclosed embodiments but is intended to cover various arrangements included within the spirit and scope of the broadest interpretation so as to encompass all such modifications and equivalent arrangements.

What is claimed is:

1. A synthesized nucleic acid, consisting of: the nucleotide sequence of SEQ ID NO.: 3.

2. A method for determining a floral morphology of an orchid, comprising:
   providing a biological sample taken from the orchid;
   isolating total RNA transcript from the biological sample;
   amplifying the total RNA transcript by reverse-transcription PCR to obtain a first cDNA product;
   amplifying the first cDNA product by PCR using a primer pair of SEQ ID NOs.: 13-14 to obtain a second cDNA product; and
   determining whether the second cDNA product comprises the synthesized nucleic acid of claim 1 or not, wherein when the second cDNA product comprises the synthesized nucleic acid of claim 1, the floral morphology is big-lip mutant.

3. The method as claimed in claim 2, wherein the biological sample is a seed, a protocorm, or a protocorm-like body.

* * * * *

SEQUENCE LISTING

<160> NUMBER OF SEQ ID NOS: 38

<210> SEQ ID NO 1
<211> LENGTH: 904
<212> TYPE: DNA
<213> ORGANISM: Phalaenopsis sp.

<400> SEQUENCE: 1

```
atgggaaggg gaagagttga gcttaagcgt atcgagaaca agatcaacag acaggtaacc    60
ttctccaagc gtcggaatgg catcatgaaa aaagcttacg agctctctgt tctctgcgat   120
gctgaaatag ctcttataat cttctccagc cgcggcaaac tcttcgagtt cggcagcccc   180
gacataacta aaacgctaga gcgctatcaa cggtgcactt ttactcctca gactatccat   240
cctaatgatc atgaaacact gaactggtat caagaattat ccaagctgaa agcaaaatat   300
gaatctctac aacgttctca aaggcatctg cttggagaag atctagactt actaaatttg   360
aaggaacttc aacaactgga agacaactt gaaacatctc tatctcaagc cagacaaaaa   420
aggacgcaga taatgttgga ccagatgaa gagctaaaga aaaggaacg ccaacttggt   480
gatattaaca agcagcttaa acataagctt ggggcagatg gtggatcgat gagagctctc   540
caaggttcct ggcggcctgc ttctggggcc aatattgata cttttcgtaa tcattcaagt   600
aacatggata cagaacccac tcttcaaatt gggaggtaca atcagtatgt tccttctgaa   660
gcaacaattc cgaggaacgg tggagctgga aacactttca tgcctggctg gggcgcagtt   720
tgagagagtt tgactgaaag cttcctgcaa tgtaatttca gctgttccgc ttctgtttaa   780
taacgtacct gtctgttgga ggcttttttt ttcctcaact tctacactat gactggttta   840
attatcaaac atatgttaat atctggtcat tgatcttgaa tatggtagtt gaagtactaa   900
atgg                                                                904
```

<210> SEQ ID NO 2
<211> LENGTH: 240
<212> TYPE: PRT
<213> ORGANISM: Phalaenopsis sp.

<400> SEQUENCE: 2

```
Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Ile Met Lys Lys Ala
            20                  25                  30

Tyr Glu Leu Ser Val Leu Cys Asp Ala Glu Ile Ala Leu Ile Ile Phe
        35                  40                  45

Ser Ser Arg Gly Lys Leu Phe Glu Phe Gly Ser Pro Asp Ile Thr Lys
    50                  55                  60

Thr Leu Glu Arg Tyr Gln Arg Cys Thr Phe Thr Pro Gln Thr Ile His
65                  70                  75                  80

Pro Asn Asp His Glu Thr Leu Asn Trp Tyr Gln Glu Leu Ser Lys Leu
                85                  90                  95

Lys Ala Lys Tyr Glu Ser Leu Gln Arg Ser Gln Arg His Leu Leu Gly
            100                 105                 110

Glu Asp Leu Asp Leu Leu Asn Leu Lys Glu Leu Gln Gln Leu Glu Arg
        115                 120                 125

Gln Leu Glu Thr Ser Leu Ser Gln Ala Arg Gln Lys Arg Thr Gln Ile
    130                 135                 140

Met Leu Asp Gln Met Glu Glu Leu Lys Lys Lys Glu Arg Gln Leu Gly
145                 150                 155                 160

Asp Ile Asn Lys Gln Leu Lys His Lys Leu Gly Ala Asp Gly Gly Ser
                165                 170                 175

Met Arg Ala Leu Gln Gly Ser Trp Arg Pro Ala Ser Gly Ala Asn Ile
            180                 185                 190

Asp Thr Phe Arg Asn His Ser Ser Asn Met Asp Thr Glu Pro Thr Leu
        195                 200                 205
```

```
Gln Ile Gly Arg Tyr Asn Gln Tyr Val Pro Ser Glu Ala Thr Ile Pro
        210                 215                 220

Arg Asn Gly Gly Ala Gly Asn Thr Phe Met Pro Gly Trp Gly Ala Val
225                 230                 235                 240
```

<210> SEQ ID NO 3
<211> LENGTH: 730
<212> TYPE: DNA
<213> ORGANISM: Phalaenopsis sp.

<400> SEQUENCE: 3

```
atgggaaggg gaagagttga gcttaagcgt atcgagaaca agatcaacag acaggtaacc      60
ttctccaagc gtcggaatgg catcatgaaa aaagcttacg agctctctgt tctctgcgat     120
gctgaaatag ctcttataat cttctccagc cgcggcaaac tcttcgagtt cggcagcccc     180
gacataacta aaacgctaga gcgctatcaa cggtgcactt ttactcctca gactatccat     240
cctaatgatc atgaaacact gaactggtat caagaattat ccaagctgaa agcaaaatat     300
gaatctctac aacgttctca aaggcatctg cttggagaag atctagactt actaaatttg     360
aaggaacttc aacaactgga agacaactt gaaacatctc tatctcaagc cagacaaaaa      420
aggacgcaga taatgttgga ccagatggaa gagctaaaga aaaaggaggt acaatcagta     480
tgttccttct gaagcaacaa ttccgaggaa cggtggagct ggaaacactt tcatgcctgg     540
ctggggcgca gtttgagaga gtttgactga agcttcctg caatgtaatt tcagctgttc       600
cgcttctgtt taataacgta cctgtctgtt ggaggctttt ttttcctca acttctacac      660
tatgactggt ttaattatca aacatatgtt aatatctggt cattgatctt gaatatggta     720
gttgaagtac                                                            730
```

<210> SEQ ID NO 4
<211> LENGTH: 163
<212> TYPE: PRT
<213> ORGANISM: Phalaenopsis sp.

<400> SEQUENCE: 4

```
Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Ile Met Lys Lys Ala
            20                  25                  30

Tyr Glu Leu Ser Val Leu Cys Asp Ala Glu Ile Ala Leu Ile Ile Phe
        35                  40                  45

Ser Ser Arg Gly Lys Leu Phe Glu Phe Gly Ser Pro Asp Ile Thr Lys
    50                  55                  60

Thr Leu Glu Arg Tyr Gln Arg Cys Thr Phe Thr Pro Gln Thr Ile His
65                  70                  75                  80

Pro Asn Asp His Glu Thr Leu Asn Trp Tyr Gln Glu Leu Ser Lys Leu
                85                  90                  95

Lys Ala Lys Tyr Glu Ser Leu Gln Arg Ser Gln Arg His Leu Leu Gly
            100                 105                 110

Glu Asp Leu Asp Leu Leu Asn Leu Lys Glu Leu Gln Gln Leu Glu Arg
        115                 120                 125

Gln Leu Glu Thr Ser Leu Ser Gln Ala Arg Gln Lys Arg Thr Gln Ile
    130                 135                 140

Met Leu Asp Gln Met Glu Glu Leu Lys Lys Lys Glu Val Gln Ser Val
145                 150                 155                 160
```

Cys Ser Phe

<210> SEQ ID NO 5
<211> LENGTH: 694
<212> TYPE: DNA
<213> ORGANISM: Phalaenopsis sp.

<400> SEQUENCE: 5

```
atgggaaggg gaagagttga gcttaagcgt atcgagaaca agatcaacag acaggtaacc      60
ttctccaagc gtcggaatgg catcatgaaa aaagcttacg agctctctgt tctctgcgat     120
gctgaaatag ctcttataat cttctccagc cgcggcaaac tcttcgagtt cggcagcccc     180
gacataacta aaacgctaga gcgctatcaa cggtgcactt ttactcctca gactatccat     240
cctaatgatc atgagacact gaactggtat caagaattat ccaagctgaa agcaaaatat     300
gaatctctac aacgttctca aaggcatctg cttggagaag atctagactt actaaatttg     360
aaggaacttc aacaactgga agacaacttt gaaacatctc tatctcaagc cagacaaaaa     420
agggaggtac aatcagtatg ttccttctga ggcaacaatt ccgaggaacg gtggagctgg     480
aaacactttc atgcctggct ggggcgcagt ttgagagagt ttgactgaaa gcttcctgca     540
atgtaatttc agctgttccg cttctgttta taacgtacc tgtctgttgg aggcttttt      600
ttcctcaact tttacactat gactggttta attatcaaac atatgttaat atctggtcat     660
taatcttgaa tatggtagtt gaagtactaa atgg                                 694
```

<210> SEQ ID NO 6
<211> LENGTH: 149
<212> TYPE: PRT
<213> ORGANISM: Phalaenopsis sp.

<400> SEQUENCE: 6

```
Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Ile Met Lys Lys Ala
            20                  25                  30

Tyr Glu Leu Ser Val Leu Cys Asp Ala Glu Ile Ala Leu Ile Ile Phe
        35                  40                  45

Ser Ser Arg Gly Lys Leu Phe Glu Phe Gly Ser Pro Asp Ile Thr Lys
    50                  55                  60

Thr Leu Glu Arg Tyr Gln Arg Cys Thr Phe Thr Pro Gln Thr Ile His
65                  70                  75                  80

Pro Asn Asp His Glu Thr Leu Asn Trp Tyr Gln Glu Leu Ser Lys Leu
                85                  90                  95

Lys Ala Lys Tyr Glu Ser Leu Gln Arg Ser Gln Arg His Leu Leu Gly
            100                 105                 110

Glu Asp Leu Asp Leu Leu Asn Leu Lys Glu Leu Gln Gln Leu Glu Arg
        115                 120                 125

Gln Leu Glu Thr Ser Leu Ser Gln Ala Arg Gln Lys Arg Glu Val Gln
    130                 135                 140

Ser Val Cys Ser Phe
145
```

<210> SEQ ID NO 7
<211> LENGTH: 599
<212> TYPE: DNA
<213> ORGANISM: Phalaenopsis sp.

<400> SEQUENCE: 7

-continued

```
atgggaaggg gaagagttga gcttaagcgt atcgagaaca agatcaacag acagccgcgg    60
caaactcttc gagttcggca gccccgacat aactaaaacg ctagagcgct atcaacggtg   120
cacttttact cctcagacta tccatcctaa tgatcatgaa acactgaact ggtatcaaga   180
attatccaag ctgaaagcaa atatgaatc tctacaacgt tctcaaaggc atctgcttgg    240
agaagatcta gacttactaa atttgaagga acttcaacaa ctggaaagac aacttgaaac   300
atctctatct caagccagac aaaaaaggga ggtacaatca gtatgttcct tctgaagcaa   360
caattccgag aacggtgga gctggaaaca ctttcatgcc tggctggggc gcagtttgag     420
agagtttgac tgaaagcttc ctgcaatgta atttcagctg ttccgcttct gtttaataac   480
gtacctgtct gttggaggct tttttttcct caacttttac actatgactg gtttaattat   540
caaacatatg ttaatatctg gtcattaatc ttgaatatgg tagttgaagt actaaatgg    599
```

<210> SEQ ID NO 8
<211> LENGTH: 31
<212> TYPE: PRT
<213> ORGANISM: Phalaenopsis sp.

<400> SEQUENCE: 8

Met Gly Arg Gly Arg Val Glu Leu Lys Arg Ile Glu Asn Lys Ile Asn
1               5                   10                  15

Arg Gln Pro Arg Gln Thr Leu Arg Val Arg Gln Pro Arg His Asn
            20                  25                  30

<210> SEQ ID NO 9
<211> LENGTH: 574
<212> TYPE: DNA
<213> ORGANISM: Phalaenopsis sp.

<400> SEQUENCE: 9

```
atgggaaggg gaagagttga gcttaagcgt atcgagaaca agatcaacag acaggtaacc    60
ttctccaagc gtcggaatgg catcatgaaa aaagcttacg agctctctgt tctctgcgat   120
gccgaaatag ctcttataat cttctccagc cgcggcaaac tcttcgagtt cggcagcccc   180
gacataacta aaacgctaga gcgctatcag cggtgcactt ttactcctca gactatccat   240
cctaatgatc atgaaacact ggcgcagata atgttggacc agatggaaga gctcaagaaa   300
aaggaggtac aatcagtatg ttccttctga ggcaacaatt ccgaggaacg gtggagctgg   360
aaacactttc atgcctggct ggggcgcagt ttgagagagt ttgactgaaa gcttcctgca   420
atgtaatttc agctgttccg cttctgttta ataacgtacc tgtctgttgg aggcttttt    480 ttcctcaact tttacactat gactggttta attatcaaac atatgttaat atctggtcat   540
taatcttgaa tatggtagtt gaagtactaa atgg                                574
```

<210> SEQ ID NO 10
<211> LENGTH: 109
<212> TYPE: PRT
<213> ORGANISM: Phalaenopsis sp.

<400> SEQUENCE: 10

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Ile Met Lys Lys Ala
            20                  25                  30

Tyr Glu Leu Ser Val Leu Cys Asp Ala Glu Ile Ala Leu Ile Ile Phe
        35                  40                  45

```
Ser Ser Arg Gly Lys Leu Phe Glu Phe Gly Ser Pro Asp Ile Thr Lys
    50                  55                  60

Thr Leu Glu Arg Tyr Gln Arg Cys Thr Phe Thr Pro Gln Thr Ile His
 65                  70                  75                  80

Pro Asn Asp His Glu Thr Leu Ala Gln Ile Met Leu Asp Gln Met Glu
                 85                  90                  95

Glu Leu Lys Lys Lys Glu Val Gln Ser Val Cys Ser Phe
            100                 105

<210> SEQ ID NO 11
<211> LENGTH: 25
<212> TYPE: DNA
<213> ORGANISM: Artificial Sequence
<220> FEATURE:
<223> OTHER INFORMATION: Synthetic

<400> SEQUENCE: 11
cgcggctgga gaagattata agagc                                    25

<210> SEQ ID NO 12
<211> LENGTH: 26
<212> TYPE: DNA
<213> ORGANISM: Artificial Sequence
<220> FEATURE:
<223> OTHER INFORMATION: Synthetic

<400> SEQUENCE: 12
agatgggaag gggaagagtt gagctt                                   26

<210> SEQ ID NO 13
<211> LENGTH: 25
<212> TYPE: DNA
<213> ORGANISM: Artificial Sequence
<220> FEATURE:
<223> OTHER INFORMATION: Synthetic

<400> SEQUENCE: 13
atgggaaggg gaagagttga gctta                                    25

<210> SEQ ID NO 14
<211> LENGTH: 27
<212> TYPE: DNA
<213> ORGANISM: Artificial Sequence
<220> FEATURE:
<223> OTHER INFORMATION: Synthetic

<400> SEQUENCE: 14
ccatttagta cttcaactac catattc                                  27

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
tgcactttta ctcctcagac tatccat                                  27

<210> SEQ ID NO 16
<211> LENGTH: 25
<212> TYPE: DNA
<213> ORGANISM: Artificial Sequence
<220> FEATURE:
```

<223> OTHER INFORMATION: Synthetic

<400> SEQUENCE: 16
gctttcagct tggataattc ttgat                                                  25

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
gctgtcttcc ccagcattgt                                                        20

<210> SEQ ID NO 18
<211> LENGTH: 22
<212> TYPE: DNA
<213> ORGANISM: Artificial Sequence
<220> FEATURE:
<223> OTHER INFORMATION: Synthetic

<400> SEQUENCE: 18
caaccattac tccggtatga cg                                                     22

<210> SEQ ID NO 19
<211> LENGTH: 259
<212> TYPE: PRT
<213> ORGANISM: Poa annua

<400> SEQUENCE: 19

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Ser Arg Gly Lys Leu Tyr Glu Phe Gly Ser Ala Gly Thr Thr Lys
    50                  55                  60

Thr Leu Glu Arg Tyr Gln His Cys Cys Tyr Asn Ala Gln Asp Ser Asn
65                  70                  75                  80

Ser Ala Leu Ser Glu Thr Gln Ser Trp Tyr Gln Glu Met Ser Lys Leu
                85                  90                  95

Lys Ala Lys Phe Glu Ala Leu Gln Arg Thr Gln Arg His Leu Leu Gly
            100                 105                 110

Glu Asp Leu Gly Pro Leu Ser Val Lys Glu Leu Gln Gln Leu Glu Lys
        115                 120                 125

Gln Leu Glu Cys Ser Leu Ser Gln Ala Arg Gln Arg Lys Thr Gln Leu
    130                 135                 140

Met Val Glu Gln Val Glu Glu Leu Arg Arg Lys Glu Arg Gln Leu Gly
145                 150                 155                 160

Glu Ile Asn Arg Gln Leu Lys His Lys Leu Asp Ala Glu Gly Ser Ser
                165                 170                 175

Ser Asn Asn Tyr Arg Ala Met Gln Gln Leu Thr Trp Ala Ala Gly Thr
            180                 185                 190

Val Val Asp Glu Gly Ala Ala Ala Tyr His Met Gln His Gln Gln Gln
        195                 200                 205

Gln Gln Pro Asn His Ser Ala Ala Met Asp Cys Glu Pro Thr Leu Gln
    210                 215                 220

```
Ile Gly Tyr Pro His Gln Phe Ala Ala Pro Glu Gln Ala Ala Asn Asn
225                 230                 235                 240

Ile Pro Arg Ser Ser Gly Gln Gly Gly Glu Asn Asn Phe Met Leu Gly
                245                 250                 255

Trp Val Leu

<210> SEQ ID NO 20
<211> LENGTH: 260
<212> TYPE: PRT
<213> ORGANISM: Lolium perenne

<400> SEQUENCE: 20

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Asp Ala Glu Val Ala Leu Ile Ile Phe
            35                  40                  45

Ser Ser Arg Gly Lys Leu Tyr Glu Phe Gly Ser Ala Gly Thr Thr Lys
    50                  55                  60

Thr Leu Glu Arg Tyr Gln His Cys Cys Tyr Asn Ala Gln Asp Ser Ser
65                  70                  75                  80

Ser Ala Leu Ser Glu Thr Gln Ser Trp Tyr Gln Glu Met Ser Lys Leu
                85                  90                  95

Lys Ala Lys Phe Glu Ala Leu Gln Arg Thr Gln Arg His Leu Leu Gly
            100                 105                 110

Glu Asp Leu Gly Pro Leu Ser Val Lys Glu Leu Gln Gln Leu Glu Lys
        115                 120                 125

Gln Leu Glu Cys Ser Leu Ser Gln Ala Arg Gln Arg Lys Thr Gln Leu
    130                 135                 140

Met Met Glu Gln Val Glu Glu Leu Arg Arg Lys Glu Arg Gln Leu Gly
145                 150                 155                 160

Glu Ile Asn Arg Gln Leu Lys His Lys Leu Asp Ala Glu Gly Ser Ser
                165                 170                 175

Ser Asn Ser Phe Arg Ala Met Gln Gln Leu Thr Trp Ala Ala Gly Thr
            180                 185                 190

Val Val Asp Glu Gly Ala Gly Ala Tyr His Met His His Gln Gln Gln
        195                 200                 205

Pro Asn His Ser Ala Ala Met Asp Cys Glu Pro Thr Leu Gln Ile Gly
    210                 215                 220

Tyr Pro His Gln Phe Ala Ala Ala Glu Gln Ala Ala Asn Asn Ile Pro
225                 230                 235                 240

Arg Ser Ser Ala Pro Gly Gly Glu Asn Asn Phe Met Leu Gly Trp Val
                245                 250                 255

Leu Gly Ala Gln
            260

<210> SEQ ID NO 21
<211> LENGTH: 243
<212> TYPE: PRT
<213> ORGANISM: Agapanthus praecox

<400> SEQUENCE: 21

Met Gly Arg Gly Arg Val Glu Leu Lys Arg Ile Glu Asn Lys Ile Asn
1               5                   10                  15
```

```
Arg Gln Val Thr Phe Ser Lys Arg Arg Asn Gly Leu Leu Lys Lys Ala
            20                  25                  30

Tyr Glu Leu Ser Val Leu Cys Asp Ala Glu Val Ala Leu Ile Val Phe
        35                  40                  45

Ser Ser Arg Gly Lys Leu Tyr Glu Phe Gly Ser Ala Gly Thr Ser Lys
 50                  55                  60

Thr Leu Glu Arg Tyr Gln Arg Cys Cys Tyr Thr Ser Gln Asp Ala Thr
 65                  70                  75                  80

Ile Ala Asp Arg Glu Lys Gln Asn Trp Tyr Gln Glu Val Ala Arg Leu
                85                  90                  95

Lys Ala Lys Phe Glu Ser Leu Gln Ser Ala Gln Arg His Leu Leu Gly
            100                 105                 110

Glu Asp Leu Gly Pro Leu Ser Val Lys Glu Leu Gln Gln Leu Glu Arg
            115                 120                 125

Gln Leu Glu Ala Ser Leu Ser Gln Ala Arg Gln Arg Lys Thr Gln Ile
            130                 135                 140

Met Phe Asp Gln Met Glu Glu Leu Arg Lys Lys Glu His His Leu Gly
145                 150                 155                 160

Glu Ile Asn Lys Gln Leu Lys Thr Lys Leu Glu Ala Glu Gly Glu Asn
                165                 170                 175

Leu Arg Ala Ile Gln Gly Ser Trp Glu Ser Asp Ala Thr Asn Val Gly
            180                 185                 190

Gly Gly Asn Val Phe Ser Met His Pro Ser His Ser Ser Ala Met Glu
            195                 200                 205

Cys Glu Pro Thr Leu Gln Ile Gly Tyr His Gln Leu Val Gln Pro Glu
210                 215                 220

Gly Ser Leu Pro Arg Asn Ser Gly Gly Glu Asn Asn Phe Met Leu Gly
225                 230                 235                 240

Trp Val Leu

<210> SEQ ID NO 22
<211> LENGTH: 242
<212> TYPE: PRT
<213> ORGANISM: Hyacinthus orientalis

<400> SEQUENCE: 22

Met Gly Arg Gly Arg Val Glu Leu Lys Arg Ile Glu Asn Lys Ile Asn
 1               5                  10                  15

Arg Gln Val Thr Phe Ser Lys Arg Arg Asn Gly Leu Leu Lys Lys Ala
            20                  25                  30

Tyr Glu Leu Ser Val Leu Cys Asp Ala Glu Val Ala Leu Ile Val Phe
        35                  40                  45

Ser Ser Arg Gly Lys Leu Tyr Glu Phe Gly Ser Ala Gly Thr Gly Lys
 50                  55                  60

Thr Leu Glu Arg Tyr Gln Arg Cys Cys Tyr Thr Ser Gln Asp Ala Ser
 65                  70                  75                  80

Ile Ala Asp Arg Glu Ala Gln Ser Trp Tyr Gln Glu Val Ser Lys Leu
                85                  90                  95

Lys Ala Lys Phe Glu Ser Leu Gln Arg Ser Gln Arg His Leu Leu Gly
            100                 105                 110

Glu Asp Leu Gly Pro Leu Ser Val Lys Glu Leu Gln Gln Leu Glu Arg
            115                 120                 125

Gln Met Glu Ser Ala Leu Ser Gln Ala Arg Gln Arg Lys Gln Thr Gln
130                 135                 140
```

-continued

```
Ile Met Leu Asp Gln Met Glu Glu Leu Arg Lys Lys Glu Arg His Leu
145                 150                 155                 160

Gly Glu Ile Asn Lys His Leu Lys Ser Arg Leu Glu Ala Glu Gly Ala
                165                 170                 175

Thr Phe Arg Ala Ile Gln Gly Ser Trp Glu Ser Thr Ala Ala Ile Gln
            180                 185                 190

Gly Asn Ala Phe Ser Val His Pro Ser Gln Ser Arg Ala Met Asp Cys
        195                 200                 205

Glu Pro Thr Leu Gln Ile Gly Tyr His His Leu Val Gln Pro Glu Glu
    210                 215                 220

Ala Ile Pro Arg Asn Thr Val Gly Glu Asn Asn Phe Met Leu Gly Trp
225                 230                 235                 240

Val Leu

<210> SEQ ID NO 23
<211> LENGTH: 241
<212> TYPE: PRT
<213> ORGANISM: Elaeis guineensis var. tenera

<400> SEQUENCE: 23

Met Gly Arg Gly Arg Val Glu Leu Lys Arg Ile Glu Asn Lys Ile Asn
1               5                   10                  15

Arg Gln Val Thr Phe Ser Lys Arg Arg Ser Gly Leu Leu Lys Lys Ala
                20                  25                  30

Tyr Glu Leu Ser Val Leu Cys Asp Ala Glu Ile Ala Leu Ile Ile Phe
            35                  40                  45

Ser Ser Arg Gly Lys Leu Tyr Glu Phe Gly Ser Val Gly Thr Ser Lys
        50                  55                  60

Thr Leu Glu Arg Tyr Gln Arg Cys Cys Tyr Thr Ser Gln Asp Ser Asn
65                  70                  75                  80

Phe Ala Asp Gln Glu Thr Gln Asn Trp Tyr Gln Glu Met Ala Lys Leu
                85                  90                  95

Lys Ala Lys Phe Glu Ser Leu Gln Arg Ser Gln Arg His Leu Leu Gly
                100                 105                 110

Glu Asp Leu Gly Pro Leu Thr Val Lys Glu Leu Gln Gln Leu Glu Arg
            115                 120                 125

Gln Leu Glu Ser Ala Leu Ser Gln Ala Arg Gln Arg Lys Ala Gln Ile
        130                 135                 140

Met Leu Asp Gln Met Glu Glu Leu Arg Lys Lys Glu Arg His Leu Gly
145                 150                 155                 160

Glu Ile Asn Lys Gln Leu Lys Asp Arg Leu Asp Ala Glu Ser Ala Ser
                165                 170                 175

Phe Arg Ala Ile Gln Gly Ser Trp Ala Ser Asp Gly Val Val Thr Asn
            180                 185                 190

Asn Ala Phe Ser Leu Gln Pro Ser Gln Ser Asn Asp Met Asp Cys Glu
        195                 200                 205

Pro Thr Leu Gln Ile Gly Phe Pro Gln Leu Val Pro Pro Glu Ala Ala
    210                 215                 220

Ile Thr Arg Asn Thr Gly Gly Glu Asn Asn Phe Met Leu Gly Trp Val
225                 230                 235                 240

Leu

<210> SEQ ID NO 24
<211> LENGTH: 233
<212> TYPE: PRT
```

<213> ORGANISM: Persea americana

<400> SEQUENCE: 24

Lys Arg Ile Glu Asn Lys Ile Asn Arg Gln Val Thr Phe Ser Lys Arg
1               5                   10                  15

Arg Asn Gly Leu Leu Lys Lys Ala Tyr Glu Leu Ser Ile Leu Cys Asp
            20                  25                  30

Ala Glu Val Ala Leu Ile Ile Phe Ser Ser Arg Gly Lys Leu Tyr Glu
        35                  40                  45

Phe Gly Ser Val Gly Thr Asn Lys Thr Leu Glu Arg Tyr Gln Arg Cys
    50                  55                  60

Cys Tyr Asn Pro Gln Asp Ala Asn Ile Ser Asp Arg Glu Thr Gln Gly
65                  70                  75                  80

Trp Tyr Gln Glu Val Ser Lys Leu Lys Ala Lys Tyr Glu Ser Leu Gln
                85                  90                  95

Arg Ser Gln Arg His Leu Leu Gly Glu Asp Leu Gly Pro Leu Ser Val
            100                 105                 110

Lys Glu Leu Gln Gln Leu Glu Arg Glu Leu Glu Val Ala Leu Ser Lys
        115                 120                 125

Ala Arg Gln Arg Lys Thr Gln Ile Met Met Glu Gln Met Glu Glu Leu
    130                 135                 140

Arg Lys Lys Glu Arg Gln Leu Gly Asp Ile Asn Lys Gln Phe Lys Asn
145                 150                 155                 160

Lys Leu Glu Ala Glu Gly Ala Phe Arg Gly Leu Gln Gly Ser Trp Glu
                165                 170                 175

Ser Gly Ala Val Val Gly Asn Asn Thr Phe Ser Leu His Pro Ser Gln
            180                 185                 190

Ser Gly Pro Met Asp Cys Glu Pro Thr Leu Gln Ile Gly Tyr His Pro
        195                 200                 205

His Phe Val Pro Pro Glu Ala Ala Ile Pro Arg Thr Val Ala Gly Glu
    210                 215                 220

Gly Asn Phe Ile Gln Gly Trp Ala Leu
225                 230

<210> SEQ ID NO 25
<211> LENGTH: 250
<212> TYPE: PRT
<213> ORGANISM: Oryza sativa subsp. japonica

<400> SEQUENCE: 25

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Ser Arg Gly Lys Leu Tyr Glu Phe Gly Ser Ala Gly Ile Thr Lys
    50                  55                  60

Thr Leu Glu Arg Tyr Gln His Cys Cys Tyr Asn Ala Gln Asp Ser Asn
65                  70                  75                  80

Asn Ala Leu Ser Glu Thr Gln Ser Trp Tyr His Glu Met Ser Lys Leu
                85                  90                  95

Lys Ala Lys Phe Glu Ala Leu Gln Arg Thr Gln Arg His Leu Leu Gly
            100                 105                 110

Glu Asp Leu Gly Pro Leu Ser Val Lys Glu Leu Gln Gln Leu Glu Lys

```
            115                 120                 125
Gln Leu Glu Cys Ala Leu Ser Gln Ala Arg Gln Arg Lys Thr Gln Leu
    130                 135                 140

Met Met Glu Gln Val Glu Glu Leu Arg Arg Lys Glu Arg Gln Leu Gly
145                 150                 155                 160

Glu Ile Asn Arg Gln Leu Lys His Lys Leu Glu Val Glu Gly Ser Thr
                165                 170                 175

Ser Asn Tyr Arg Ala Met Gln Gln Ala Ser Trp Ala Gln Gly Ala Val
            180                 185                 190

Val Glu Asn Gly Ala Ala Tyr Val Gln Pro Pro His Ser Ala Ala
        195                 200                 205

Met Asp Ser Glu Pro Thr Leu Gln Ile Gly Tyr Pro His Gln Phe Val
    210                 215                 220

Pro Ala Glu Ala Asn Thr Ile Gln Arg Ser Thr Ala Pro Ala Gly Ala
225                 230                 235                 240

Glu Asn Asn Phe Met Leu Gly Trp Val Leu
                245                 250

<210> SEQ ID NO 26
<211> LENGTH: 241
<212> TYPE: PRT
<213> ORGANISM: Crocus sativus

<400> SEQUENCE: 26

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Asp Ala Glu Val Ala Leu Ile Ile Phe
            35                  40                  45

Ser Ser Arg Gly Lys Leu Tyr Glu Phe Gly Ser Ala Gly Thr Pro Lys
        50                  55                  60

Thr Leu Glu Arg Tyr Gln Arg Cys Cys Tyr Thr Ser Gln Asp Ser Thr
65                  70                  75                  80

Ile Ala Asp Arg Glu Thr Gln Ser Trp Tyr Gln Glu Val Ser Lys Leu
                85                  90                  95

Lys Ala Lys Phe Glu Ser Leu Gln Arg Ser Gln Arg His Leu Leu Gly
                100                 105                 110

Glu Asp Leu Gly Pro Leu Ser Val Lys Glu Leu Gln Gln Leu Glu Arg
            115                 120                 125

Gln Leu Glu Ser Ala Leu Ser Gln Ala Arg Gln Arg Lys Thr Gln Ile
    130                 135                 140

Met Leu Asp Gln Met Glu Glu Leu Arg Lys Lys Glu Arg His Leu Gly
145                 150                 155                 160

Glu Ile Asn Lys Gln Leu Lys Asn Lys Leu Glu Thr Glu Gly Ser Thr
                165                 170                 175

Phe Arg Ala Phe Gln Gly Ser Trp Glu Ser Asp Gly Val Val Gly Ser
            180                 185                 190

Asn Ala Phe Pro Ile His Pro Ser Gln Ser Ser Ala Met Asp Cys Glu
        195                 200                 205

Pro Thr Leu Gln Ile Gly Tyr His His Leu Val Gln Pro Glu Thr Ala
    210                 215                 220

Leu Pro Arg Asn Ser Ala Gly Glu Asn Asn Phe Met Leu Gly Trp Val
225                 230                 235                 240
```

Leu

<210> SEQ ID NO 27
<211> LENGTH: 241
<212> TYPE: PRT
<213> ORGANISM: Crocus sativus

<400> SEQUENCE: 27

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Ser Arg Gly Lys Leu Tyr Glu Phe Gly Ser Ala Gly Thr Pro Lys
    50                  55                  60

Thr Leu Glu Arg Tyr Gln Arg Cys Cys Tyr Thr Ser Gln Asp Ser Thr
65                  70                  75                  80

Ile Ala Asp Arg Glu Thr Gln Ser Trp Tyr Gln Glu Val Ser Lys Leu
                85                  90                  95

Lys Ala Lys Phe Glu Ser Leu Gln Arg Ser Gln Arg His Leu Leu Gly
            100                 105                 110

Glu Asp Leu Gly Pro Leu Ser Val Lys Glu Leu Gln Gln Leu Glu Arg
        115                 120                 125

Gln Leu Glu Ser Ser Leu Ser Gln Ala Arg Gln Arg Lys Thr Gln Ile
    130                 135                 140

Met Leu Asp Gln Met Glu Glu Leu Arg Lys Lys Glu Arg His Leu Gly
145                 150                 155                 160

Glu Leu Asn Asn Gln Leu Lys Asn Lys Leu Glu Thr Glu Gly Ser Thr
                165                 170                 175

Phe Arg Ala Ile Gln Gly Ser Trp Glu Ser Asn Gly Gly Val Gly Asn
            180                 185                 190

Asn Ala Phe Pro Phe His Pro Ser Gln Ser Ser Ala Met Asp Cys Glu
        195                 200                 205

Pro Thr Leu Gln Ile Gly Tyr His His Leu Val Gln Pro Glu Thr Val
    210                 215                 220

Leu Pro Arg Ile Ser Glu Gly Glu Asn Asn Phe Met Val Gly Trp Val
225                 230                 235                 240

Leu

<210> SEQ ID NO 28
<211> LENGTH: 240
<212> TYPE: PRT
<213> ORGANISM: Bambusa oldhamii

<400> SEQUENCE: 28

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

Tyr Glu Leu Ser Val Leu Cys Asp Val Glu Val Ala Leu Ile Val Phe
        35                  40                  45

Ser Ser Arg Gly Lys Leu Tyr Glu Phe Gly Ser Ala Gly Thr Ser Lys
    50                  55                  60

Thr Leu Glu Arg Tyr Gln Arg Cys Cys Tyr Ser Ser Gln Asp Gly Thr
65                  70                  75                  80

Val Ala Asp Arg Glu Met Gln Ser Trp Tyr Gln Val Ser Lys Leu
            85                  90                  95

Lys Ala Lys Phe Glu Ser Leu Gln Arg Ser Gln Arg His Leu Leu Gly
                100                 105                 110

Glu Asp Leu Gly Pro Leu Ser Ile Lys Glu Leu Gln Gln Leu Glu Gly
            115                 120                 125

Gln Leu Glu Ser Ser Leu Ser Gln Ala Arg Gln Arg Lys Thr Gln Ile
130                 135                 140

Met Leu Asp Gln Met Glu Glu Leu Arg Lys Lys Glu Arg Arg Leu Gly
145                 150                 155                 160

Glu Ile Asn Lys Gln Leu Lys Thr Lys Leu Glu Gln Glu Gly Ala Asn
                165                 170                 175

Leu Gly Ala Ile Gln Ser Ser Trp Glu Ala Glu Ala Val Gly Asn
            180                 185                 190

Ser Tyr Gln Ile His Leu Gly Gln Ser Ser Ala Met Asp Cys Glu Pro
    195                 200                 205

Thr Leu Gln Ile Gly Tyr His Gln Phe Val Gln Pro Glu Ala Gly Leu
    210                 215                 220

Pro Arg Asn Thr Gly Gly Glu Asn Asn Phe Met Leu Gly Trp Val Leu
225                 230                 235                 240

<210> SEQ ID NO 29
<211> LENGTH: 241
<212> TYPE: PRT
<213> ORGANISM: Narcissus tazetta var. chinensis

<400> SEQUENCE: 29

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Asp Ala Glu Val Ala Leu Ile Val Phe
            35                  40                  45

Ser Ser Arg Gly Lys Leu Tyr Glu Phe Gly Ser Ala Gly Thr Ser Lys
50                  55                  60

Thr Leu Glu Arg Tyr Gln Arg Cys Cys Tyr Thr Ser Gln Asp Ala Ala
65                  70                  75                  80

Ile Ala Asp Arg Glu Thr Gln Asn Trp Cys His Glu Val Ser Lys Leu
                85                  90                  95

Lys Ala Lys Phe Glu Ser Leu Gln Arg Ser Gln Arg His Leu Leu Gly
                100                 105                 110

Glu Asp Leu Gly Pro Leu Ser Ile Lys Glu Leu Gln Gln Leu Glu Arg
            115                 120                 125

Gln Leu Glu Ala Ser Leu Ser Gln Ala Arg Gln Arg Lys Thr Gln Ile
130                 135                 140

Met Leu Asp Gln Met Glu Glu Leu Arg Arg Lys Glu Arg His Leu Gly
145                 150                 155                 160

Glu Ile Asn Lys Gln Leu Lys Ile Lys Leu Glu Gln Glu Gly Ala Asn
                165                 170                 175

Leu Gly Ala Ile Gln Ser Ser Trp Glu Ala Glu Ala Ala Val Gly Gly
            180                 185                 190

Asn Ser Tyr Gln Ile His Leu Gly Gln Ser Ser Ala Met Asp Cys Glu
        195                 200                 205

Pro Thr Leu Gln Ile Gly Tyr His Gln Phe Val Gln Pro Glu Ala Gly

```
                 210                 215                 220

Leu Pro Arg Asn Thr Gly Gly Glu Asn Asn Phe Met Leu Gly Trp Val
225                 230                 235                 240

Leu

<210> SEQ ID NO 30
<211> LENGTH: 250
<212> TYPE: PRT
<213> ORGANISM: Oryza sativa subsp. indica

<400> SEQUENCE: 30

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Asp Ala Glu Val Ala Leu Ile Ile Phe
            35                  40                  45

Ser Ser Arg Gly Lys Leu Tyr Glu Phe Gly Ser Ala Gly Ile Thr Lys
    50                  55                  60

Thr Leu Glu Arg Tyr Gln His Cys Cys Tyr Asn Ala Gln Asp Ser Asn
65                  70                  75                  80

Asn Ala Leu Ser Glu Thr Gln Ser Trp Tyr His Glu Leu Ser Lys Leu
                85                  90                  95

Lys Ala Lys Phe Glu Ala Leu Gln Arg Thr Gln Arg His Leu Leu Gly
            100                 105                 110

Glu Asp Leu Gly Pro Leu Ser Val Lys Glu Leu Gln Gln Leu Glu Lys
        115                 120                 125

Gln Leu Glu Cys Ala Leu Ser Gln Ala Arg Gln Arg Lys Thr Gln Leu
    130                 135                 140

Met Met Glu Gln Val Glu Glu Leu Arg Arg Lys Glu Arg Gln Leu Gly
145                 150                 155                 160

Glu Ile Asn Arg Gln Leu Lys His Lys Leu Glu Val Glu Gly Ser Thr
                165                 170                 175

Ser Asn Tyr Arg Ala Met Gln Gln Ala Ser Trp Ala Gln Gly Ala Val
            180                 185                 190

Val Glu Asn Gly Ala Ala Tyr Val Gln Pro Pro His Ser Ala Ala
        195                 200                 205

Met Asp Ser Glu Pro Thr Leu Gln Ile Gly Tyr Pro His Gln Phe Val
    210                 215                 220

Pro Ala Glu Ala Asn Thr Ile Gln Arg Ser Thr Ala Pro Ala Gly Ala
225                 230                 235                 240

Glu Asn Asn Phe Met Leu Gly Trp Val Leu
                245                 250

<210> SEQ ID NO 31
<211> LENGTH: 241
<212> TYPE: PRT
<213> ORGANISM: Chimonanthus praecox

<400> SEQUENCE: 31

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Asp Ala Glu Val Ala Leu Ile Ile Phe
            35                  40                  45
```

```
Ser Ser Arg Gly Lys Leu Tyr Glu Phe Gly Ser Val Gly Thr Ile Lys
    50                  55                  60

Thr Leu Glu Arg Tyr Gln Arg Cys Cys Tyr Asn Pro Gln Asp Ala Asn
 65                  70                  75                  80

Thr Ser Asp Arg Glu Thr Gln Ala Trp Tyr Gln Glu Val Ser Lys Leu
                 85                  90                  95

Lys Val Lys Tyr Glu Ser Leu Gln Arg Ser Gln Arg His Leu Leu Gly
                100                 105                 110

Glu Asp Leu Gly Pro Leu Ser Val Arg Glu Leu Gln Asn Leu Glu Lys
            115                 120                 125

Gln Leu Glu Val Ala Leu Ser Gln Ala Arg Gln Arg Lys Thr Gln Ile
130                 135                 140

Met Met Glu Gln Met Glu Glu Leu Arg Arg Lys Glu Arg Gln Leu Gly
145                 150                 155                 160

Asp Ile Asn Lys Gln Leu Arg Asn Lys Leu Glu Ala Gly Gln Gly Ala
                165                 170                 175

Leu Arg Ser Ile Gln Gly Gln Trp Glu Ser Gly Ala Ile Val Gly Asn
            180                 185                 190

Asn Thr Phe Ser Leu His Pro Ser His Ser Ser His Ile Glu Cys Glu
        195                 200                 205

Pro Thr Leu Gln Ile Gly Tyr Pro Gln Phe Val Pro Pro Glu Ala Thr
210                 215                 220

Ile Pro Arg Ser Ala Pro Gly Glu Asn Asn Phe Met Arg Gly Trp Val
225                 230                 235                 240

Leu

<210> SEQ ID NO 32
<211> LENGTH: 244
<212> TYPE: PRT
<213> ORGANISM: Vitis vinifera

<400> SEQUENCE: 32

Met Gly Arg Gly Arg Val Glu Leu Lys Arg Ile Glu Asn Lys Ile Asn
 1                   5                  10                  15

Arg Gln Val Thr Phe Ser Lys Arg Arg Asn Gly Leu Leu Lys Lys Ala
                20                  25                  30

Tyr Glu Leu Ser Val Leu Cys Asp Ala Glu Val Ala Leu Ile Ile Phe
            35                  40                  45

Ser Ser Arg Gly Lys Leu Tyr Glu Phe Gly Ser Ala Gly Thr Thr Lys
    50                  55                  60

Thr Leu Glu Arg Tyr Gln Arg Val Cys Tyr Thr Pro Gln Asp Asn Asn
 65                  70                  75                  80

Met Glu Cys Glu Thr Gln Ser Trp Tyr Gln Glu Val Ser Lys Leu Lys
                 85                  90                  95

Ala Lys Tyr Glu Ser Leu Gln Arg Thr Gln Arg His Leu Leu Gly Glu
                100                 105                 110

Asp Leu Gly Pro Leu Ser Val Lys Glu Leu Gln Asn Leu Glu Lys Gln
            115                 120                 125

Leu Glu Gly Ala Leu Ala Gln Ala Arg Gln Arg Lys Thr Gln Met Met
130                 135                 140

Ile Glu Gln Met Glu Asp Leu Arg Arg Lys Glu Arg Gln Leu Gly Asp
145                 150                 155                 160

Leu Asn Lys Gln Leu Lys Leu Lys Leu Glu Ala Glu Gly Gln Ser Leu
                165                 170                 175
```

Lys Ala Ile Gln Gly Ser Trp Asn Pro Ser Thr Ala Thr Ala Gly Asn
            180                 185                 190

Ser Ser Phe Pro Val His Pro Ser Gln Ser Asn Pro Met Asp Cys Glu
        195                 200                 205

Pro Glu Pro Ile Leu Gln Ile Gly Tyr His His Tyr Val Pro Ala Glu
210                 215                 220

Gly Pro Ser Val Ser Lys Ser Met Ala Gly Glu Ser Asn Phe Ile Gln
225                 230                 235                 240

Gly Trp Val Leu

<210> SEQ ID NO 33
<211> LENGTH: 246
<212> TYPE: PRT
<213> ORGANISM: Nuphar advena

<400> SEQUENCE: 33

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

Tyr Glu Leu Ser Val Leu Cys Asp Ala Glu Val Ala Leu Ile Val Phe
        35                  40                  45

Ser Ser Arg Gly Lys Leu Tyr Glu Phe Gly Ser Ala Gly Leu Ser Lys
    50                  55                  60

Thr Ile Glu Arg Tyr Gln Arg Cys Asn Tyr Asn Pro Leu Asp Asn Asn
65                  70                  75                  80

Ile Ser Val Arg Glu Thr Gln Asn Trp Tyr Gln Glu Val Ala Lys Leu
                85                  90                  95

Lys Ala Arg Tyr Glu Ala Leu Gln Arg Ser Gln Arg His Leu Leu Gly
            100                 105                 110

Glu Asp Leu Gly Pro Leu Ser Val Lys Glu Leu Gln Gln Leu Glu Arg
        115                 120                 125

Gln Leu Glu Thr Ala Leu Ser Gln Ala Arg Gln Arg Lys Thr Gln Ile
    130                 135                 140

Met Met Glu Gln Met Asp Glu Leu Arg Lys Lys Glu Arg His Leu Gly
145                 150                 155                 160

Asp Val Asn Lys Gln Leu Lys Asn Gln Leu Glu Ser Gln Gly His Val
                165                 170                 175

Phe Arg Ser Met Pro Gly Ser Ser Ser Ser Trp Glu Ser Gly Val Val
            180                 185                 190

Val Gly Asn Asn Ser Leu Asn Met Asn Ala Ala Gln Val Asp His Ile
        195                 200                 205

Asp Cys Glu Pro Thr Leu Gln Ile Gly Tyr His Gln Phe Val Pro Pro
    210                 215                 220

Asp Gly Thr Ser Asn Ile Ala Arg Thr Val Ala Ala Glu Asn Asn Phe
225                 230                 235                 240

Ile Gln Gly Trp Ile Leu
                245

<210> SEQ ID NO 34
<211> LENGTH: 240
<212> TYPE: PRT
<213> ORGANISM: Oncidium hybrid cultivar

<400> SEQUENCE: 34

```
Met Gly Arg Gly Arg Val Glu Leu Lys Arg Ile Glu Asn Lys Ile Asn
1               5                   10                  15

Arg Gln Val Thr Phe Ser Lys Arg Asn Gly Ile Met Lys Lys Ala
            20                  25                  30

Tyr Glu Leu Ser Val Leu Cys Asp Ala Glu Ile Ala Leu Ile Ile Phe
            35                  40                  45

Ser Ser Arg Gly Lys Leu Phe Glu Phe Gly Ser Pro Asp Ile Thr Lys
50                  55                  60

Thr Leu Glu Arg Tyr Arg Arg Cys Thr Phe Thr Pro Gln Thr Ile His
65                  70                  75                  80

Pro Asn Asp His Glu Thr Leu Asn Trp Tyr Gln Glu Leu Ser Lys Leu
                85                  90                  95

Lys Ala Lys Tyr Glu Ser Leu Gln Arg Ser Gln Arg His Leu Leu Gly
                100                 105                 110

Glu Asp Leu Asp Met Leu Ser Leu Lys Glu Leu Gln Gln Leu Glu Arg
            115                 120                 125

Gln Leu Glu Ser Ser Leu Ser Gln Ala Arg Gln Lys Arg Thr Gln Ile
    130                 135                 140

Met Leu His Gln Met Asp Glu Leu Lys Lys Lys Glu Arg His Leu Gly
145                 150                 155                 160

Asp Ile Asn Lys Gln Leu Lys His Lys Leu Gly Ala Asn Gly Gly Ser
                165                 170                 175

Ser Arg Ala Leu Gln Gly Ser Asn Trp Gln Pro Asp Gly Gly Ala Gly
            180                 185                 190

Met Glu Thr Phe Arg Asn His Ser Asn Asn Met Asp Thr Glu Pro Thr
            195                 200                 205

Leu Gln Ile Gly Arg Tyr Asn Gln Tyr Val Ser Ser Glu Ala Thr Ile
    210                 215                 220

Ser Arg Asn Gly Gly Ala Gly Asn Ser Phe Met Ser Gly Trp Ala Val
225                 230                 235                 240

<210> SEQ ID NO 35
<211> LENGTH: 242
<212> TYPE: PRT
<213> ORGANISM: Oncidium hybrid cultivar

<400> SEQUENCE: 35

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

Tyr Glu Leu Ser Val Leu Cys Asp Ala Glu Val Ala Leu Ile Ile Phe
            35                  40                  45

Ser Ser Arg Gly Lys Leu Tyr Glu Phe Gly Ser Ala Gly Thr Cys Lys
50                  55                  60

Thr Leu Glu Arg Tyr Gln His Ser Cys Tyr Ser Ser Gln Ala Thr Asn
65                  70                  75                  80

Ser Ile Asp Arg Glu Thr Gln Ser Trp Tyr Gln Glu Val Ser Lys Leu
                85                  90                  95

Lys Thr Lys Phe Glu Thr Leu Gln Arg Ser His Arg Asn Leu Leu Gly
                100                 105                 110

Glu Asp Leu Gly Pro Leu Asn Val Lys Glu Leu Gln Gln Leu Glu Arg
            115                 120                 125

Gln Leu Glu Thr Ala Leu Ser Gln Ala Arg Gln Arg Lys Thr Gln Ile
    130                 135                 140
```

```
Met Leu Asp Gln Met Glu Glu Leu Arg Lys Lys Glu Arg Gln Leu Gly
145                 150                 155                 160

Glu Leu Asn Lys Gln Leu Lys Met Lys Leu Glu Ala Gly Gly Ser Ser
                165                 170                 175

Leu Arg Leu Met Gln Gly Ser Trp Glu Ser Asp Thr Val Val Asp Gly
            180                 185                 190

Asn Ala Phe Gln Met His Pro Phe Pro Ser Ser Ser Leu Glu Cys Glu
                195                 200                 205

Pro Ala Leu His Ile Gly Tyr His Gln Phe Val Pro Pro Glu Thr Val
            210                 215                 220

Ile Ala Arg Thr Pro Gly Val Glu Asn Ser Asn Phe Met Leu Gly Trp
225                 230                 235                 240

Met Leu

<210> SEQ ID NO 36
<211> LENGTH: 245
<212> TYPE: PRT
<213> ORGANISM: Epimedium sagittatum

<400> SEQUENCE: 36

Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
                20                  25                  30

Tyr Glu Leu Ser Val Leu Cys Asp Ala Glu Val Gly Leu Ile Ile Phe
            35                  40                  45

Ser Ser Arg Gly Lys Leu Tyr Glu Phe Ala Ser Ala Gly Met Asn Arg
50                  55                  60

Thr Leu Glu Arg Tyr Gln Arg Cys Cys Tyr Thr Pro Gln Glu Ser Asn
65                  70                  75                  80

Leu Ala Asp Arg Glu Thr Gln Ser Trp Tyr Gln Glu Val Ser Lys Leu
                85                  90                  95

Lys Ala Lys Tyr Glu Ser Leu Gln Arg Ser Gln Arg His Leu Leu Gly
            100                 105                 110

Glu Asp Leu Gly Pro Leu Ser Val Lys Glu Leu Gln Asn Leu Glu Lys
        115                 120                 125

Gln Leu Glu Gly Ala Leu Thr Gln Ala Arg Gln Arg Lys Thr Gln Met
    130                 135                 140

Met Ile Glu Gln Met Glu Glu Leu Arg Arg Lys Glu Arg His Leu Gly
145                 150                 155                 160

Asp Ile Asn Lys Gln Leu Lys Asn Lys Phe Gln Leu Glu Ser Glu Gly
                165                 170                 175

Gln Ala Ser Gln Phe Arg Ala Ile Gln Gly Ser Trp Glu Ser Ala Ala
            180                 185                 190

Leu Val Gln Ala Asn Ser Phe Gln Gly His Pro Ser His Ser Gly Ala
        195                 200                 205

Met Asp Cys Glu Pro Thr Leu Gln Ile Gly Tyr His Asn Phe Val Pro
    210                 215                 220

Gln Glu Gly Gly Asn Val Gln Arg Thr Val Glu Glu Asn Asn Tyr Ile
225                 230                 235                 240

Gln Gly Trp Val Leu
                245

<210> SEQ ID NO 37
```

<211> LENGTH: 241
<212> TYPE: PRT
<213> ORGANISM: Alstroemeria ligtu subsp. ligtu

<400> SEQUENCE: 37

```
Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Ile Leu Lys Lys Ala
            20                  25                  30

Tyr Glu Leu Ser Val Leu Cys Asp Ala Glu Val Ala Leu Ile Ile Phe
        35                  40                  45

Ser Ser Arg Gly Lys Leu Tyr Glu Phe Gly Ser Ala Gly Thr Ser Lys
    50                  55                  60

Thr Leu Glu Arg Tyr Gln Arg Cys Cys Tyr Thr Ser Gln Asp Thr Asn
65                  70                  75                  80

Ala Ile Asp Arg Glu Thr Gln Asn Trp Tyr Gln Glu Met Ser Lys Leu
                85                  90                  95

Lys Ala Lys Phe Glu Ser Leu Gln Arg Ala Gln Arg His Leu Leu Gly
            100                 105                 110

Glu Asp Leu Gly Pro Leu Ser Val Lys Glu Leu Gln Gln Leu Glu Arg
        115                 120                 125

Gln Leu Glu Ser Ala Leu Ala Gln Ala Arg Gln Arg Lys Thr Gln Leu
    130                 135                 140

Met Leu Asp Gln Met Glu Leu Arg Lys Lys Glu Arg His Leu Gly
145                 150                 155                 160

Glu Ile Asn Lys Gln Leu Lys Asn Lys Leu Glu Ala Glu Gly Ala Asn
                165                 170                 175

Leu Arg Ala Leu Gln Gly Ser Trp Glu Ser Glu Ala Val Ala Gly Gly
            180                 185                 190

Asn Ala Phe Pro Met His Gln Ile Gln Ser Ser Ala Met Asp Thr Glu
        195                 200                 205

Pro Thr Leu Gln Ile Gly Tyr His Pro Phe Ile Pro Gln Asp Ala Asn
    210                 215                 220

Leu Gln Arg Asn Asn Gly Gly Glu Asn Asn Phe Met Leu Gly Trp Val
225                 230                 235                 240

Leu
```

<210> SEQ ID NO 38
<211> LENGTH: 245
<212> TYPE: PRT
<213> ORGANISM: Nymphaea hybrid cultivar

<400> SEQUENCE: 38

```
Met Gly Arg Gly Arg Val Glu Leu Lys Arg Ile Glu Asn Lys Ile Asn
1               5                   10                  15

Arg Gln Val Thr Phe Ser Lys Arg Arg Asn Gly Leu Leu Lys Lys Ala
            20                  25                  30

Tyr Glu Leu Ser Val Leu Cys Asp Ala Glu Val Ala Leu Ile Ile Phe
        35                  40                  45

Ser Ser Arg Gly Lys Leu Tyr Glu Phe Gly Ser Ala Gly Met Ser Lys
    50                  55                  60

Thr Leu Glu Arg Tyr Gln Arg Cys Asn Tyr Asn Pro Leu Asp Asn Thr
65                  70                  75                  80

Thr Ala Ala Arg Glu Thr Gln Asn Trp Tyr Gln Glu Val Val Lys Leu
                85                  90                  95
```

-continued

```
Lys Ala Arg Tyr Glu Ala Leu Gln Arg Ser Gln Arg His Leu Leu Gly
            100                 105                 110

Glu Asp Leu Gly Pro Leu Ser Val Lys Glu Leu Gln Gln Leu Glu Arg
        115                 120                 125

Gln Leu Glu Thr Ala Leu Ser Gln Ala Arg Gln Arg Lys Thr Gln Ile
        130                 135                 140

Met Met Glu Gln Met Asp Glu Leu Arg Lys Lys Glu Arg His Leu Gly
145                     150                 155                 160

Asp Val Asn Lys Gln Leu Lys Ser Gln Leu Glu Ser Glu Gly His Val
                165                 170                 175

Phe Arg Ser Ile Gln Gly Ser Ser Ser Trp Glu Ser Gly Val Val Val
            180                 185                 190

Ala Asn Ser Ser Phe Asn Val Asn Ala Pro Gln Ala Ser Gln Ile Asp
        195                 200                 205

Cys Glu Pro Thr Leu Gln Ile Gly Tyr His Gln Phe Val Pro Gln Asp
        210                 215                 220

Gln Asn Ala Ser Ile Ala Arg Ser Val Ala Pro Glu Asn Asn Phe Val
225                 230                 235                 240

Gln Gly Trp Val Leu
                245
```